(12) United States Patent
Siedenburg

(10) Patent No.: US 11,867,847 B2
(45) Date of Patent: ***Jan. 9, 2024

(54) LOW-NOISE POWER SOURCES FOR IMAGING SYSTEMS

(71) Applicant: Everett Scientific LLC, Everett, WA (US)

(72) Inventor: Clinton Siedenburg, Everett, WA (US)

(73) Assignee: Everett Scientific LLC, Everett, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,449

(22) Filed: Dec. 16, 2022

(65) Prior Publication Data
US 2023/0120083 A1    Apr. 20, 2023

Related U.S. Application Data

(63) Continuation of application No. 16/947,873, filed on Aug. 21, 2020, now Pat. No. 11,536,819.
(Continued)

(51) Int. Cl.
*G01S 7/52*     (2006.01)
*H02M 1/08*     (2006.01)
(Continued)

(52) U.S. Cl.
CPC ...... *G01S 7/52077* (2013.01); *G01S 7/52096* (2013.01); *G01S 15/895* (2013.01);
(Continued)

(58) Field of Classification Search
CPC ............. G01S 7/52077; G01S 7/52096; G01S 15/895; H02M 1/08; H02M 1/0045; H03F 3/45174

See application file for complete search history.

(56) References Cited

U.S. PATENT DOCUMENTS 8,287,455 B2   10/2012   Phung
8,829,905 B2   9/2014    Davila et al.
(Continued)

FOREIGN PATENT DOCUMENTS

AU   2018210232 B2   2/2022
CA      3050694 A1   7/2018
(Continued)

OTHER PUBLICATIONS

Semtech Corporation, SC221 20MHz, 650mA, X-EMI-Enabled Synchronous Step-Down Regulator, Product Brochure, 2016, 14 pages.

*Primary Examiner* — Daniel Pihulic
(74) *Attorney, Agent, or Firm* — FORTEM IP LLP; Matthew Lincicum

(57) ABSTRACT

Power supplies for electronic devices (e.g. medical imaging devices) are disclosed herein. In one embodiment, a switched mode power supply is minimized in size and weight while maintaining efficiency and an artifact-free image using power supply design techniques tailored to increasing the power conversion frequency to be above the desired receive band of an ultrasound imaging system. In another embodiment, a switched mode power supply is minimized in size and weight while maintaining efficiency and an artifact-free image using power supply design techniques tailored to increasing the power conversion frequency to be just below the desired receive band of an ultrasound imaging system causing the third harmonic and possibly the second harmonic to fall just above the desired receive band.

20 Claims, 16 Drawing Sheets

Related U.S. Application Data

(60) Provisional application No. 62/894,595, filed on Aug. 30, 2019.

(51) Int. Cl.
*G01S 15/89* (2006.01)
*H03F 3/45* (2006.01)
*H02M 1/00* (2006.01)

(52) U.S. Cl.
CPC ............ *H02M 1/08* (2013.01); *H02M 1/0045* (2021.05); *H03F 3/45174* (2013.01)

(56) References Cited

U.S. PATENT DOCUMENTS

| | | |
|---|---|---|
| 8,937,475 B2 | 1/2015 | Malaney et al. |
| 11,166,637 B2 | 11/2021 | Siedenburg |
| 11,536,819 B2 * | 12/2022 | Siedenburg ........... G01S 15/895 |
| 2008/0287789 A1 | 11/2008 | Hwang et al. |
| 2009/0018442 A1 | 1/2009 | Miller et al. |
| 2017/0065182 A1 | 3/2017 | Wang et al. |
| 2018/0199834 A1 | 7/2018 | Siedenburg |
| 2019/0014997 A9 | 1/2019 | Siedenburg |
| 2019/0046163 A1 | 2/2019 | Siedenburg |
| 2021/0059646 A1 * | 3/2021 | Siedenburg ......... G01S 7/52096 |
| 2022/0061684 A1 | 3/2022 | Siedenburg |

FOREIGN PATENT DOCUMENTS

| | | |
|---|---|---|
| EP | 3570737 | 11/2019 |
| JP | 2008-011925 A | 1/2008 |
| JP | 2018-108142 A | 7/2018 |
| WO | 2018/136135 A1 | 7/2018 |
| WO | 2018/136656 A1 | 7/2018 |

* cited by examiner

LOW-NOISE POWER SOURCES FOR IMAGING SYSTEMS

CROSS-REFERENCE TO RELATED APPLICATION

This application is a continuation of U.S. patent application Ser. No. 16/947,873, filed Aug. 21, 2020, which claims priority to U.S. Provisional Patent Application No. 62/894,595, filed Aug. 30, 2019, each of which is hereby incorporated by reference in its entirety.

TECHNICAL FIELD

The disclosed technology relates generally to electric power sources for imaging electronic devices and systems, and in particular to compact, efficient, and low noise power sources for portable ultrasound imaging devices.

BACKGROUND

Many portable electronic devices include switching power supplies, or switched-mode power supplies, (SMPS) (e.g. DC-to-DC converters) having a circuit topology (e.g., flyback, buck, boost, buck-boost, etc.) with one or more large and relatively dense passive components (e.g., an inductor or transformer). The switching power supply circuits can be bulky and may consume a relatively large area or volume of the imaging device. Some ultrasound systems devote about half of the circuitry just to create low-noise power sources for the imaging function. Although generally much more efficient than the use of linear regulators, switching power supplies can also be inefficient, particularly if, for example, a cascade of DC-to-DC converters is used to generate voltages on multiple rails. Moreover, switching power supplies can generate electromagnetic interference and switching harmonics, which can produce noise in an image (e.g., ultrasound B-mode image) formed by a system connected to the power supply. Mitigation of switching power supply noise sources may require using extensive countermeasures such as, for example, synchronization of the switching supplies to the acquisition timing (e.g., for sensitive Doppler imaging) and/or extensive passive filtering and shielding in cascade with one or more low dropout linear regulators (e.g., with B-mode imaging). Despite good design practices, often half the power converted escapes as heat in the power conversion and noise mitigation circuits. Given these problems and others, a need exists for a simpler, more efficient circuit method and configuration that produces supply voltages with minimal image noise and creation of heat.

SUMMARY

The subject technology is illustrated, for example, according to various aspects described below, including with reference to FIGS. 1-6I. Various examples of aspects of the subject technology are described as numbered clauses (1, 2, 3, etc.) for convenience. These are provided as examples and do not limit the subject technology.

Clause 1. An imaging system comprising:
a transducer having a sensitivity band with an upper limit $F_{XDCR-UPPER}$;
signal processing circuitry configured to receive output signals from the transducer; and
a switched mode power supply configured to provide power to one or more components of the signal processing circuitry, the switched mode power supply configured to operate at a switching rate $F_{SMPS}$;
wherein $F_{SMPS}$ is greater than $F_{XDCR-UPPER}$.

Clause 2. The system of claim 1, further comprising an analog-to-digital converter (ADC) configured to receive and digitize the output signals from the signal processing circuitry, the ADC configured to operate at an ADC rate $F_{ADC}$;
wherein $F_{ADC}$ is an integer multiple of $F_{SMPS}$.

Clause 3. The system of any one of the Clauses herein, wherein the ADC is synchronized with the switched mode power supply.

Clause 4. The system of any one of the Clauses herein, wherein the signal processing circuitry comprises at least one of: a transmit/receive switch or an amplifier.

Clause 5. The system of any one of the Clauses herein, wherein $F_{SMPS}$ is greater than a bandwidth of the transducer.

Clause 6. The system of any one of the Clauses herein, wherein the transducer sensitivity band has a lower limit $F_{XDCR-LOWER}$, and wherein $F_{SMPS}$ is within about 100 kHz, about 200 kHz, about 300 kHz, about 400 kHz, about 500 kHz, about 600 kHz, about 700 kHz, about 800 kHz, about 900 kHz, about 1 MHz, about 1.5 MHz, or about 2 MHz of $F_{XDCR-LOWER}$.

Clause 7. The system of any one of the Clauses herein, wherein the transducer has a bandwidth of between about 1 and about 15 MHz.

Clause 8. The system of any one of the Clauses herein, wherein the transducer has a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 9. The system of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

Clause 10. The system of any one of the Clauses herein, wherein the transducer is an ultrasound transducer.

Clause 11. An imaging system comprising:
a transducer having a sensitivity band with a lower limit $F_{XDCR-LOWER}$ and an upper limit $F_{XDCR-UPPER}$;
signal processing circuitry configured to receive output signals from the transducer;
a switched mode power supply configured to provide power to one or more components of the signal processing circuitry, the switched mode power supply configured to operate at a switching rate $F_{SMPS}$;
wherein $F_{SMPS}$ is less than $F_{XDCR-LOWER}$ and the second harmonic of $F_{SMPS}$ is greater than $F_{XDCR-UPPER}$.

Clause 12. The system of any one of the Clauses herein, further comprising an analog-to-digital converter (ADC) configured to receive and digitize the output signals from the signal processing circuitry, the ADC configured to operate at an ADC rate $F_{ADC}$; wherein $F_{ADC}$ is an integer multiple of $F_{SMPS}$.

Clause 13. The system of any one of the Clauses herein, wherein the ADC is synchronized with the switched mode power supply.

Clause 14. The system of any one of the Clauses herein, wherein the signal processing circuitry comprises at least one of: a transmit/receive switch or an amplifier.

Clause 15. The system of any one of the Clauses herein, wherein $F_{SMPS}$ is greater than a bandwidth of the transducer.

Clause 16. The system of any one of the Clauses herein, wherein $F_{SMPS}$ is within about 100 kHz, about 200 kHz, about 300 kHz, about 400 kHz, about 500 kHz, about 600 kHz, about 700 kHz, about 800 kHz, about 900 kHz, about 1 MHz, about 1.5 MHz, or about 2 MHz of $F_{XDCR\text{-}LOWER}$.

Clause 17. The system of any one of the Clauses herein, wherein the transducer has a bandwidth of between about 1 and about 15 MHz.

Clause 18. The system of any one of the Clauses herein, wherein the transducer has a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 19. The system of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

Clause 20. The system of any one of the Clauses herein, wherein the transducer is an ultrasound transducer.

Clause 21. An imaging system comprising:
a transducer having a sensitivity band with a lower limit $F_{XDCR\text{-}LOWER}$ and an upper limit $F_{XDCR\text{-}UPPER}$;
signal processing circuitry configured to receive output signals from the transducer;
a switched mode power supply configured to provide power to one or more components of the signal processing circuitry, the switched mode power supply configured to operate at a switching rate $F_{SMPS}$;
wherein $F_{SMPS}$ is less than $F_{XDCR\text{-}LOWER}$ and the third harmonic of $F_{SMPS}$ is greater than $F_{XDCR\text{-}UPPER}$.

Clause 22. The system of any one of the Clauses herein, further comprising an analog-to-digital converter (ADC) configured to receive and digitize the output signals from the signal processing circuitry, the ADC configured to operate at an ADC rate $F_{ADC}$; wherein $F_{ADC}$ is an integer multiple of $F_{SMPS}$.

Clause 23. The system of any one of the Clauses herein, wherein the ADC is synchronized with the switched mode power supply.

Clause 24. The system of any one of the Clauses herein, wherein the signal processing circuitry comprises at least one of: a transmit/receive switch or an amplifier.

Clause 25. The system of any one of the Clauses herein, wherein $F_{SMPS}$ is greater than a bandwidth of the transducer.

Clause 26. The system of any one of the Clauses herein, wherein $F_{SMPS}$ is within about 100 kHz, about 200 kHz, about 300 kHz, about 400 kHz, about 500 kHz, about 600 kHz, about 700 kHz, about 800 kHz, about 900 kHz, about 1 MHz, about 1.5 MHz, or about 2 MHz of $F_{XDCR\text{-}LOWER}$.

Clause 27. The system of any one of the Clauses herein, wherein the transducer has a bandwidth of between about 1 and about 15 MHz.

Clause 28. The system of any one of the Clauses herein, wherein the transducer has a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 29. The system of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

Clause 30. The system of any one of the Clauses herein, wherein the transducer is an ultrasound transducer.

Clause 31. An imaging system comprising:
a transducer having a sensitivity band with a lower limit $F_{XDCR\text{-}LOWER}$;
signal processing circuitry configured to receive output signals from the transducer; and
a switched mode power supply configured to provide power to one or more components of the signal processing circuitry, the switched mode power supply configured to operate at a switching rate $F_{SMPS}$;
wherein $F_{SMPS}$ is within about 1 MHz of $F_{XDCR\text{-}LOWER}$.

Clause 32. The system of any one of the Clauses herein, further comprising an analog-to-digital converter (ADC) configured to receive and digitize the output signals from the signal processing circuitry, the ADC configured to operate at an ADC rate $F_{ADC}$, wherein $F_{ADC}$ is an integer multiple of $F_{SMPS}$.

Clause 33. The system of any one of the Clauses herein, wherein the ADC is synchronized with the switched mode power supply.

Clause 34. The system of any one of the Clauses herein, wherein the signal processing circuitry comprises at least one of: a transmit/receive switch or an amplifier.

Clause 35. The system of any one of the Clauses herein, wherein $F_{SMPS}$ is greater than a bandwidth of the transducer.

Clause 36. The system of any one of the Clauses herein, wherein $F_{SMPS}$ is within about 100 kHz, about 200 kHz, about 300 kHz, about 400 kHz, about 500 kHz, about 600 kHz, about 700 kHz, about 800 kHz, about 900 kHz, about 1 MHz, about 1.5 MHz, or about 2 MHz of $F_{XDCR\text{-}LOWER}$.

Clause 37. The system of any one of the Clauses herein, wherein the transducer has a bandwidth of between about 1 and about 15 MHz.

Clause 38. The system of any one of the Clauses herein, wherein the transducer has a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 39. The system of any one of the Clauses herein, wherein $F_{SMPS}$ is greater than a bandwidth of the transducer.

Clause 40. The system of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

Clause 41. The system of any one of the Clauses herein, wherein the transducer is an ultrasound transducer.

Clause 42. A signal processing device comprising:
one or more transducers having an upper band limit of $F_{XDCR\text{-}UPPER}$;
a transmit/receive switch coupled to the transducer(s);
an analog receive path coupled to the transmit/receive switch, the analog receive path including an amplifier configured to amplify the signal level;
an analog-to-digital converter coupled to the amplifier and configured to digitize the amplified signal;
one or more switched mode power supplies operating at a switching rate $F_{SMPS}$ providing power to at least one of: the amplifier or the transmit/receive switch;
an analog-to-digital converter (ADC) coupled to the analog receive path, the ADC operating at an ADC rate $F_{ADC}$ which is an integer multiple of $F_{SMPS}$;
wherein $N*F_{SMPS}$ is above the upper band limit $F_{XDCR\text{-}UPPER}$, wherein N is 1, 2, or 3.

Clause 43. The device of any one of the Clauses herein, wherein the ADC is synchronized to the switched mode power supply.

Clause 44. The device of any one of the Clauses herein, wherein the transducer has a bandwidth of between about 1 and about 15 MHz.

Clause 45. The system of any one of the Clauses herein, wherein the transducer has a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 46. The system of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

Clause 47. The system of any one of the Clauses herein, wherein the transducer is an ultrasound transducer.

Clause 48. A switched mode power supply controller configured to provide:
one or more sawtooth waveforms operating at about 5 MHz or above;
one or more output gate drive signals having a rise time or a fall time of less than about 10 nanoseconds;
one or more output gate drive signals that periodically pulses at a repetition frequency of about 5 MHz or higher;
one or more input clock signals that operate at about 5 MHz or higher; and
a feedback input configured to respond to signals of greater than about 1 kHz.

Clause 49. The controller of any one of the Clauses herein, wherein the controller comprises an application-specific integrated circuit (ASIC).

Clause 50. The controller of any one of the Clauses herein, further comprising an AC coupled differential amplifier configured to operate as at least one of: (i) a comparator, (ii) a level shifter, or (iii) an OR, NOR, AND, NAND or NOT gate.

Clause 51. A switched mode power supply controller comprising:
a sawtooth waveform generator configured to output waveforms having a frequency of about 5 MHz or greater; and
a gate driver configured to output gate drive signals having (1) a rise or fall time of less than about 10 nanoseconds, and (ii) a pulse repetition frequency of about 5 MHz or greater.

Clause 52. A switched mode power supply controller comprising:
a sawtooth waveform generator configured to output waveforms having a frequency of about 5 MHz or greater; and
a gate driver configured to output gate drive signals having a rise or fall time of less than about 10 nanoseconds.

Clause 53. A switched mode power supply controller comprising:
a sawtooth waveform generator configured to output waveforms having a frequency of about 5 MHz or greater; and
a gate driver configured to output gate drive signals having a pulse repetition frequency of about 5 MHz or greater.

Clause 54. The controller of any one of the Clauses herein, wherein the controller is configured to receive a clock input signal having a frequency of about 5 MHz or greater.

Clause 55. The controller of any one of the Clauses herein, wherein the controller is configured to receive a feedback input signal.

Clause 56. The controller of any one of the Clauses herein, wherein the feedback input signal comprises a voltage feedback signal from a feedback network.

Clause 57. The controller of any one of the Clauses herein, wherein the feedback input signal comprises a current feedback signal from a power conversion stage.

Clause 58. The controller of any one of the Clauses herein, wherein the sawtooth waveform generator is configured to output waveforms having a frequency of about 5 MHz, about 7 MHz, about 8 MHz, about 9 MHz, about 10 MHz, about 11 MHz, about 12 MHz, about 13 MHz, about 14 MHz, or about 15 MHz.

Clause 59. The controller of any one of the Clauses herein, wherein the a gate driver is configured to output gate drive signals having a pulse repetition frequency of about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 60. The controller of any one of the Clauses herein, wherein the controller comprises an application-specific integrated circuit (ASIC).

Clause 61. The controller of any one of the Clauses herein, further comprising an AC coupled differential amplifier configured to operate as at least one of: (i) a comparator, (ii) a level shifter, or (iii) an OR, NOR, AND, NAND or NOT gate.

Clause 62. A method comprising: operating a system or device of any one of the Clauses herein.

Clause 63. A method comprising:
obtaining image data via one or more imaging transducers having a sensitivity band with upper limit of $F_{XDCR-UPPER}$;
processing the image data via signal processing circuitry; and
powering at least a portion of the signal processing circuitry via a switched mode power supply operating at a switching rate $F_{SMPS}$,
wherein $N*F_{SMPS}$ is greater than $F_{XDCR-UPPER}$, and wherein N is 1, 2, or 3.

Clause 64. The method of any one of the Clauses herein, wherein the signal processing circuitry comprises at least one of: a transmit/receiver switch operably coupled to the transducer(s), an amplifier, or an analog-to-digital converter.

Clause 65. The method of any one of the Clauses herein, wherein the one or more imaging transducers comprise one or more ultrasound transducers.

Clause 66. The method of any one of the Clauses herein, wherein the signal processing circuitry comprises an analog-to-digital converter (ADC), the method further comprising operating the ADC in synchrony with the switched mode power supply.

Clause 67. The method of any one of the Clauses herein, wherein the one or more imaging transducers have a bandwidth of between about 1 and about 15 MHz.

Clause 68. The method of any one of the Clauses herein, wherein the one or more imaging transducers have a bandwidth of greater than about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, or about 15 MHz.

Clause 69. The method of any one of the Clauses herein, wherein $F_{SMPS}$ is greater than about 5 MHz, about 6 MHz, about 7 MHz, 8 MHz, about 9 MHz, about 10 MHz, about 11 MHz, about 12 MHz, about 13 MHz, about 14 MHz, or about 15 MHz.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The technology disclosed herein relates to improvements for electrical power supplies for electronic imaging devices processing low-level signals. Although the technology is described with respect to its use with ultrasound imaging systems, it will be appreciated that the technology can also be used in any other suitable electronic device such as, for example, mobile devices, tablets, laptop computers, smart phones, smart watches, other imaging systems (e.g., MRI, positron emission tomography, computed tomography, X-ray), etc. The disclosed technology offers several advantages over typical power supplies used in many portable electronic devices such as, for example, reduced energy losses (e.g., heat generation), simpler configurations, fewer parts, reduced noise in an image produced by the device (e.g., an ultrasound device), and/or elimination of heavy, bulky, interference-radiating components (e.g. inductors or transformers).

An electrical power supply configured in accordance with the present disclosure can, for example, provide for one or more of the following benefits: (i) minimizing or reducing power supply area, volume, and weight; (ii) maximizing or increasing efficiency of power supply artifact mitigations (less heat); (iii) minimizing or reducing the interference of one switched mode power supply upon another; (iv) minimizing or reducing switching artifacts in an image; (v) maximizing or increasing resilience to shock and vibration; and/or (vi) minimizing or reducing cost of development (fewer circuits) and construction (fewer components).

Figure 1:
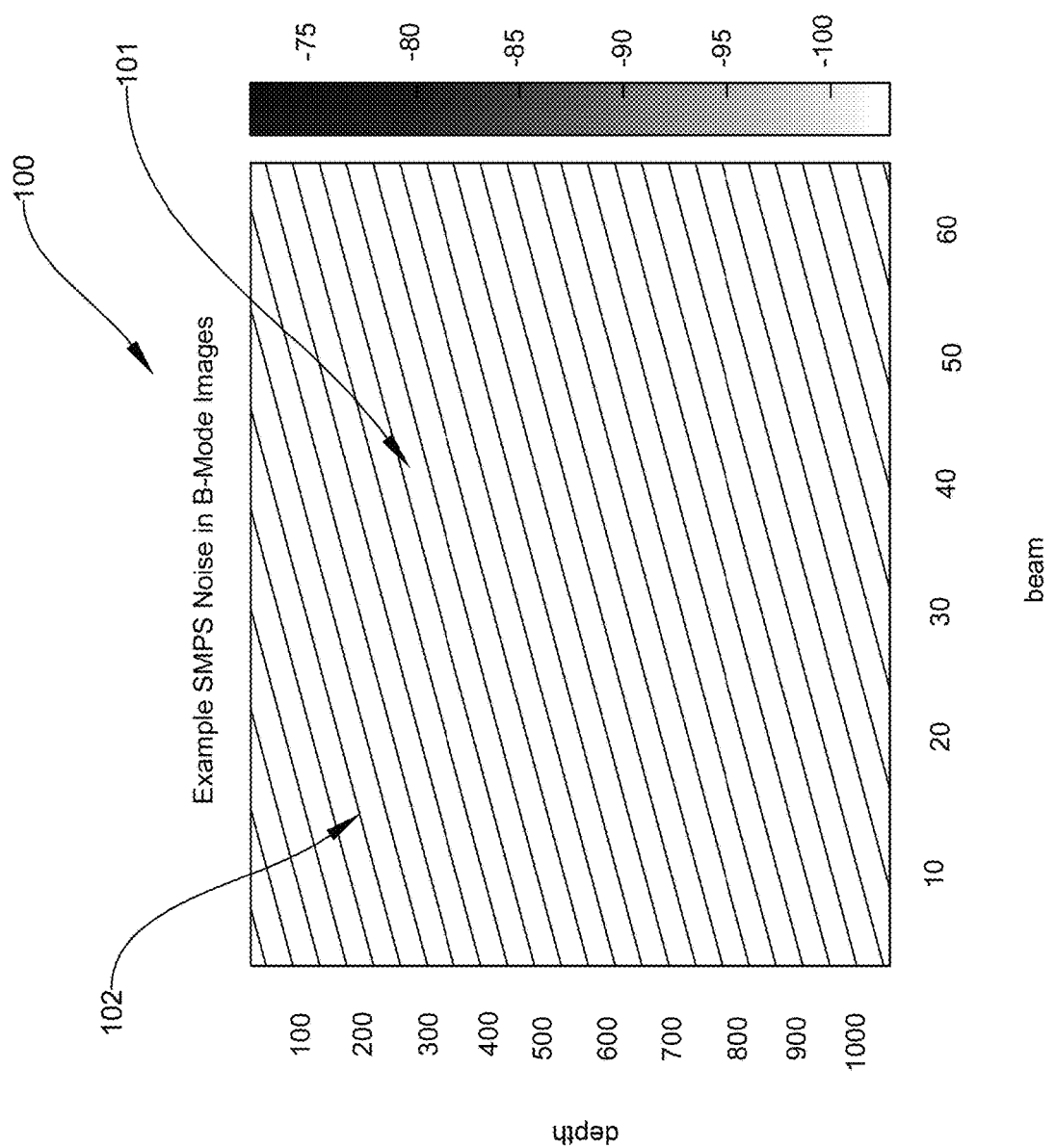
FIG. 1 illustrates the effect of power supply noise artifact in an ultrasound B-mode image.

FIG. 1 illustrates the effect of unmitigated switched mode power supply (SMPS) noise in an ultrasound image. Ultrasound display 100 contains an ultrasound image 101. Typical SMPS circuits used in imaging systems convert power at a frequency of around a few hundred kilohertz. Ultrasound imaging systems use sensors with operating bands in the few to tens of megahertz. Because SMPS switching requires steep edges, their harmonics, of which there may be hundreds, typically pass through the ultrasound band of interest, thereby producing artifacts 102, which may appear as diagonal lines across the ultrasound image 101. As described in more detail below, embodiments of the present technology can reduce or eliminate such artifacts by, for example, moving the SMPS frequency (and/or its harmonics) outside of the ultrasound band of interest.

Figure 2:
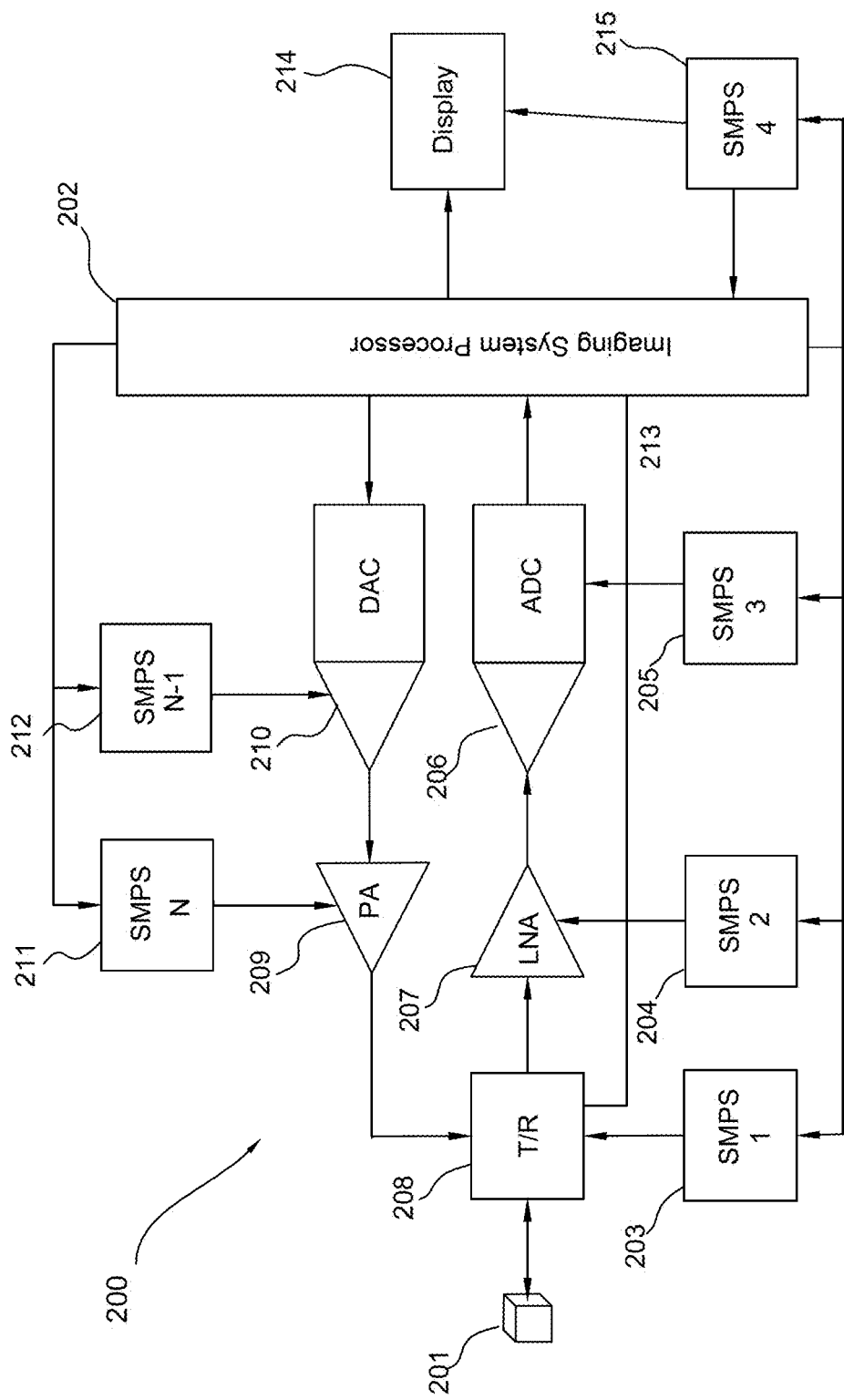
FIG. 2 illustrates the salient blocks of an imaging system affected by power supply noise artifacts.

FIG. 2 shows a generic imaging system 200. In operation, the imaging system processor 202 configures the transmit/receive switch (T/R) 208 for transmit mode with a control signal 213. The processor 202 then sends a digital control signal to a digital-to-analog converter (DAC) 210 that then feeds an analog signal to power amplifier (PA) 209. The signal from PA 209 passes through the configured T/R switch 208 to stimulate the transducer 201 causing it to radiate energy, such as ultrasound energy. Alternatively, a transducer dedicated for transmit could be used instead, eliminating a T/R switch.

The processor 202 then places T/R 208 in receive mode with control signal 213. Transducer 201 converts reflected energy, such as ultrasound mechanical energy into electrical energy and passes it through T/R 208 to the low noise amplifier (LNA) 207 which amplifies the signal for digitization by analog-to-digital converter (ADC) 206. Alternatively, a transducer dedicated for receive could be used, eliminating the T/R switch. Digitized signal imaging data is then processed by the imaging system via the processor 202 for viewing on display 214. It should be appreciated by those of skill in the art that the diagram does not denote all components necessary for an imaging system. The components depicted here simply give context to the introduction of switching noise into a front end of an example imaging system 200. Furthermore, some functions performed digitally could also be performed by analog means. Nothing lacking or which could be performed by a different way by any other suitable means should be construed as a limitation of the scope of this disclosure. Furthermore, functions depicted in FIG. 2 may be implemented in multiple ways by suitable components and by groups of components. There is not a necessary one-to-one relationship of functions to components. For example, the imaging system processor 202 may be implemented as multiple processing components, such as one for display and another for orchestrating the transmission and acquisition of signals, and perhaps another, for processing the acquired signals. Furthermore, these processing blocks may be of different types such as a CPU, GPU, FPGA, ASIC, and so forth.

Supporting this imaging functionality is a plurality of power supply rails which supply power at particular voltages to the low-voltage analog circuitry for the receive path (e.g. 208, 207), the high voltage analog circuitry for the transmit path (e.g. 209, 208), digital power for the serial interfaces of these analog blocks, analog and digital power for the ADC 206 and DAC 210, and digital power for the imaging system processor 202 and display 214. These voltage rails come from a plurality of SMPS (e.g. 203, 204, 205, 211, 212, 215). It should be appreciated by those of skill in the art that the diagram does not denote all voltages necessary for an imaging system. Typical imaging systems may have about 20 voltage rails depending upon the choices of components used to build it owing to the various core voltages and input/output (I/O) interface voltages that are required as well as the number of ground domains in the system architecture. In various embodiments, an imaging system may have any number of SMPSs configured in accordance with the present technology.

Imaging system 200 may be particularly sensitive to noise that enters as common to all channels at and before the LNA 207, and to a lesser degree as well to noise entering after the LNA 207. This is because SMPS noise is not only amplified by the LNA 207 but is also amplified by the beamforming process of the imaging system processor 202. Therefore, SMPS noise on voltage rails supplying power to T/R switch 208, LNA 207 and PA 209 tend to be the most sensitive. As those of skill in the art will appreciate, there are many other paths for SMPS noise to enter the front end from other SMPS not listed. Much depends upon layout of printed circuit board assemblies (PCBA), ground loops, and parasitic capacitances between the PCBA and housing structures.

Figure 3A:
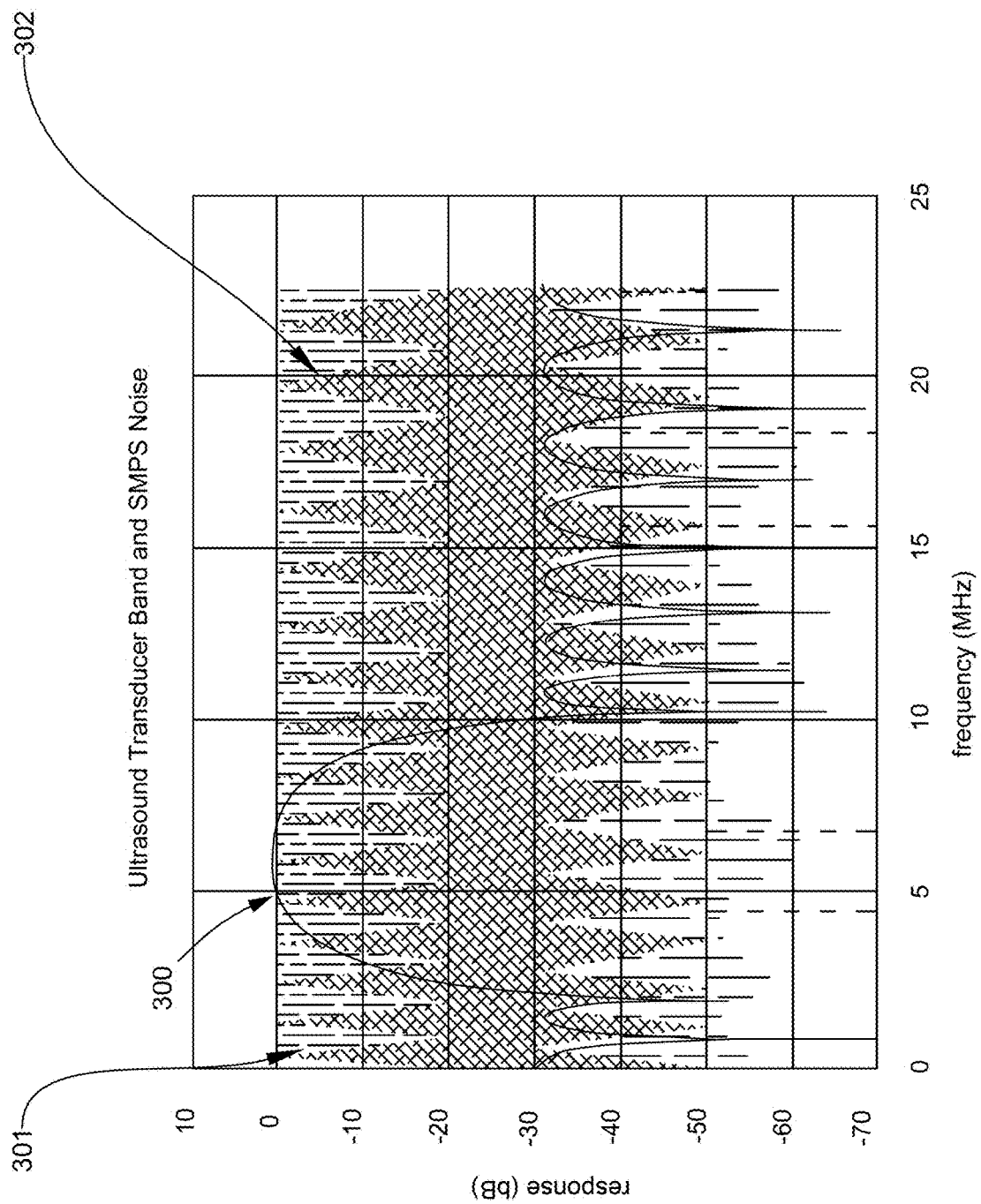
FIG. 3A illustrates the overlapping frequency content of conventional switched mode power supply (SMPS) noise relative to the ultrasound band.

An example of the SMPS noise of conventional imaging systems can be seen in FIG. 3A, in which the transducer receive band 300, SMPS fundamental switching frequency 301, and SMPS switching harmonics 302 overlap. As discussed further below, in order to mitigate the artifacts in the band of the transducer, the levels of the in-band energy can be reduced so that they are sufficiently below the imaging signals of interest and preferably below the noise floor of the image. Such mitigations are what makes the power supplies of conventional imaging systems inefficient. As used herein, the bandwidth of a transducer (e.g., an imaging transducer such as an ultrasound transducer) is the range of frequencies over which the transduction of radiated energy to electrical energy and vice versa (which can be described as a transfer function) is relatively close to its peak efficiency. Such a bandwidth can include a −6 dB bandwidth (e.g., the range of frequencies over which its amplitude, as a converter of sound energy to electrical energy or vice versa, is more than one-quarter of its maximum). Sometimes it is useful to use a −3 dB bandwidth (half energy) or −10 dB bandwidth (1/10 energy) or even a first null in the transduction transfer function.

In conventional imaging systems, the reason for selection of conversion frequencies in the range of about 100 kHz to 1 MHz is the difficulty in finding components from which to create an SMPS that operates higher than this frequency range. Above this range, parasitic capacitance and inductance inherent to the components of the SMPS or its layout degrade efficiency, thereby creating excessive heat and current draw. These parasitics also limit the frequency of operation of SMPS circuits to lower frequencies which, in turn, set the size of inductors and transformers used in the design to be larger than otherwise desired, making the implementation much less than optimal. As a result, conventional imaging systems face an undesirable trade-off between reducing size and creating heat when reducing imaging artifacts associated with SMPS noise.

Figure 3B:
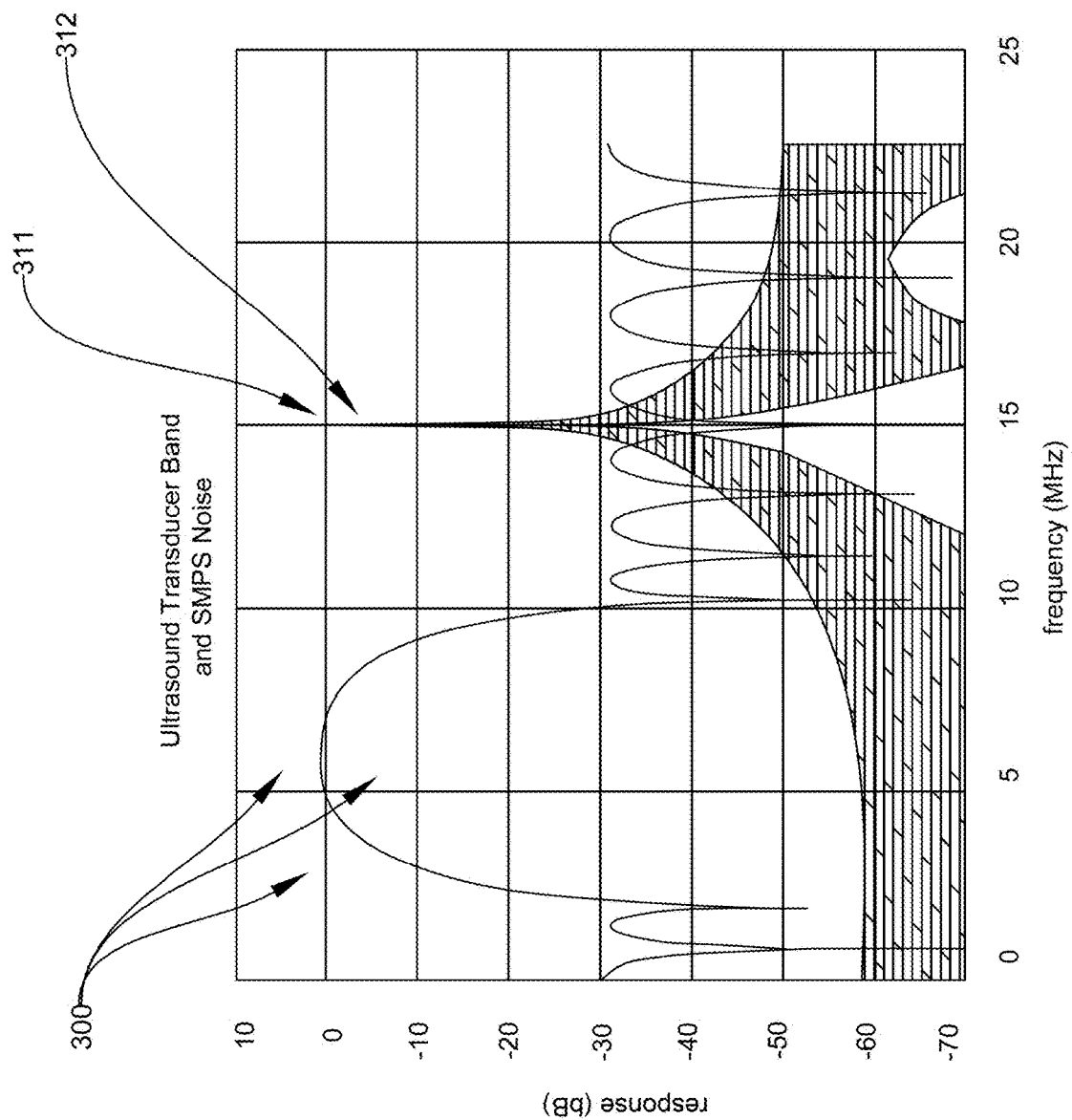
FIG. 3B illustrates the relationship of the frequency content of noise associated with an SMPS of the present technology relative to the ultrasound band.

To address these and other shortcomings, in embodiments of the present technology, the SMPS conversion frequency can be moved to be out of the desired imaging band. As shown in FIG. 3B, by moving the SMPS conversion frequency 311 to be above the band of the ultrasound sensor 300, the inherent interference is substantially eliminated. It should be appreciated by those of skill in the art that by constraining the analog-to-digital conversion (ADC) frequency to be N times the SMPS switching fundamental frequency, where N is an integer, all harmonics 312 that are beyond the ADC sample rate and which are not sufficiently attenuated by the antialiasing filter, fall upon the existing harmonic locations (e.g. the fundamental 311) in the non-aliased band. For example, if SMPS fundamental 311 having a frequency of 15 MHz has harmonics of 30 MHz, 45 MHz, and 60 MHz, the digitization process operating at 45 MHz aliases the energy of 30 MHz to −15 MHz, 45 MHz to 0 Hz, 60 MHz to 15 MHz and so on for higher positive frequencies. The negative side of the spectrum yields similar locations according to theory well known to those of skill in the art. Accordingly, harmonics appear at 0 and ±15 MHz both in the aliased and non-aliased bands, since the ADC conversion frequency (45 MHz) is an integer multiple of the SMPS fundamental switching frequency (15 MHz).

Figure 3C:
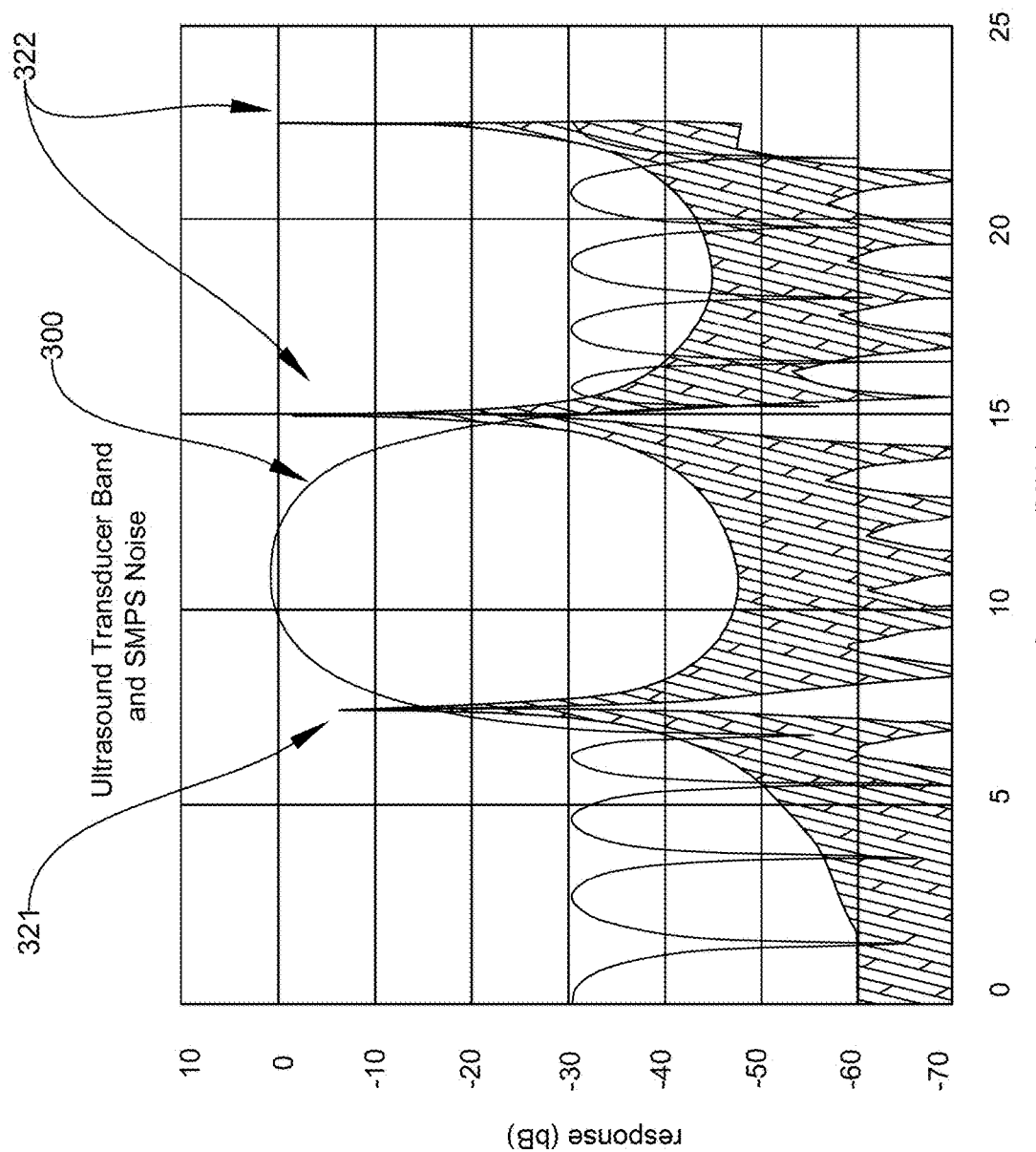
FIG. 3C illustrates another relationship of the frequency content of the noise associated with an SMPS of the present technology relative to the ultrasound band.

FIG. 3C illustrate another embodiment of the present technology. Here, rather than moving the SMPS fundamental conversion frequency to be above the transducer band, the SMPS fundamental conversion frequency 321 is moved to be below the ultrasound transducer band 300. However, because the bandwidth 300 of the ultrasound transducer is less than fundamental SMPS conversion frequency, by positioning the SMPS fundamental conversion frequency 321 just below the transducer band 300, the harmonics 322 fall above the ultrasound band 300. This is because harmonics 322 fall at frequencies that are integer multiples of the fundamental conversion frequency 321. By constraining the analog-to-digital conversion (ADC) frequency to be N times the SMPS switching fundamental frequency, all harmonics 312 that are beyond half the ADC frequency and which are not sufficiently attenuated by the antialiasing filter, fall upon the existing harmonic locations (e.g. 321 and 322) or 0 MHz (DC) in the non-aliased band. As discussed above with respect to FIG. 3B when the ADC conversion frequency (FADC) is tied to the SMPS switching frequency (FSMPS), say by an integer N, and all the harmonics of FSMPS are inherently related to FSMPS by an integer, M, then harmonics of the SMPS outside the fundamental ADC band are aliased by subtracting N*FADC from M*FSMPS with the correct integer N so that the result lands between −FADC/2 and FADC/2. Similarly, the negative harmonics that are outside this fundamental band are aliased by adding N*FSMPS to M*FSMPS with the correct integer N so that the results lands between −FADC/2 and FADC/2. The result is that all SMPS harmonics lie in the same location as the SMPS harmonics originally between −FADC/2 and FADC/2 or at DC so that no harmonics land in the imaging band 300.

In instances in which the bandwidth 300 is not less than FSMPS, the SMPS fundamental conversion frequency 321 can be positioned just below the transducer band 300 since it is the strongest signal. One or more of harmonics 322 will fall at frequencies that are integer multiples of this fundamental but still within the ultrasound band 300. For rectangular pulses, the even harmonics are much reduced, yet not perfectly absent, and a notch filter can be added to the SMPS output to attenuate the second harmonic—provided the third harmonic is above the transducer band 300. Since ultrasound transducers typically have a bandwidth less than about 100% of center frequency, there will typically be only one harmonic to attenuate using this approach.

It will be appreciated by those of skill in the art that it is not necessarily sufficient to only keep the spectral side lobes of the SMPS switching noise low enough to not create an artifact in the imaging band. It is also important to ensure that the SMPS switching noise is low enough (albeit outside the transducer band but still within the imaging system band) so that the front-end analog electronics do not become saturated with out of band noise and unable to properly condition the signal in the band of interest as well as lose its own power supply noise rejection capability.

Figure 4:
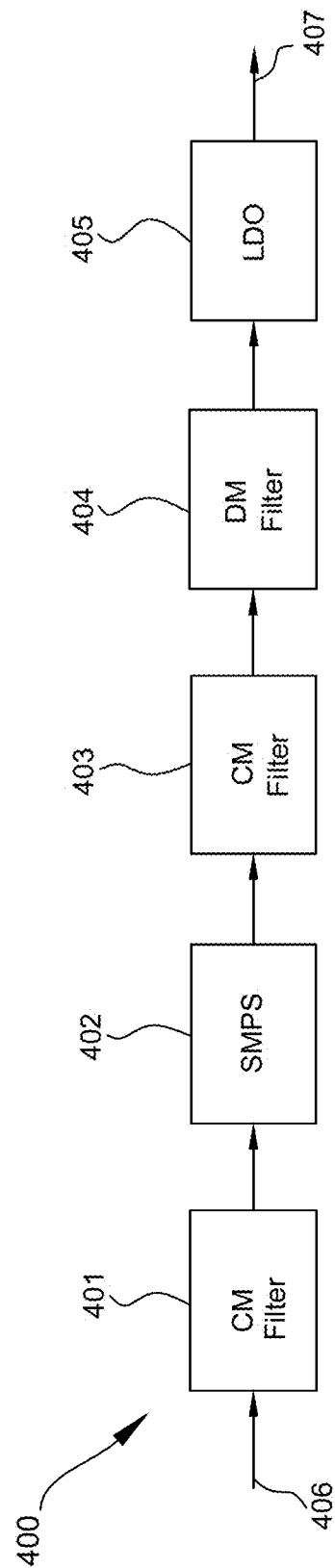
FIG. 4 illustrates the salient blocks of an SMPS in accordance with embodiments of the present technology.

FIG. 4 illustrates the basic components of an example SMPS approach 400 which is elucidated here to aid in understanding the importance of the advantages of the present technology.

The SMPS 402 functions to efficiently convert a predominantly direct current (DC) input power at one voltage (e.g., input voltage 406) to an output power of another DC voltage (e.g., output voltage 407). In cases where the input voltage is significantly larger than the output voltage, often an SMPS circuit is chosen since the wasted power is too great to use a linear regulator. In other cases, where the input voltage is lower than the output, an SMPS must be used. In either case the operation of the SMPS creates switching noise at the input and output of 402.

The resulting switching noise produced at the input can cause problems at the input of another SMPS attached to the same input voltage. In order to mitigate this, a common mode filter (CMF) 401 (containing at least a dual choke typically wired so that the magnetic fields of the forward and returning currents cancel) as is well-known to those of skill in the art is placed at the input to an SMPS to reduce and mitigate this effect to an acceptable level. CMF 401 may also have capacitors before and/or after the dual choke.

CMF 403 is added to reduce the amplitude of the output switching noise of SMPS 402 conducted to subsequent blocks making the job of artifact clean up easier. Having CMF 401 and CMF 403 bookending SMPS 402 helps to keep high frequency currents within the local SMPS ground plane.

Differential mode filter (DMF) 404 is a standard low pass filter designed to reduce the artifact content on the voltage rail. It is typically made up as one or more stages consisting of a series resistor, series inductor, and shunt capacitor (RLC) circuits. In some embodiments, the resistor can be placed in the shunt leg in series with the capacitor. This has the benefit of reducing power losses and voltage drops as the series leg carries the bulk DC current whereas the shunt leg carries only ripple current. The disadvantage is that it may not be as effective at reducing the Q of the LC circuit in that position as it is in the series position. But since embodiments of the present technology use a much higher SMPS switching frequency, the LC resonance can be placed between the planned SMPS harmonics.

The low drop out (LDO) block 405 can be a linear regulator that is designed to operate with a low voltage drop from the input to the output. It may be referenced to a voltage of sufficient precision so that the output voltage 407 is maintained despite load and line variations. But often, a few to many tenths of volts drop across it are required in order to achieve the desired artifact rejection as the pass transistor works much better when not in saturation. Since currents are high through these few to several tenths of volts drop, efficiency is significantly impacted, especially when the desired voltage rail is in the 1V to 2V range.

With this in mind, it can be seen that, beyond the benefits in moving the switching harmonics out of band, by moving to a higher frequency, the magnetic components (e.g. used in SMPS, CMF, and DMF) can all be smaller, roughly scaling linearly in each dimension with the ratio of the increase in SMPS switching frequencies. Thus, area is reduced by the frequency ratio squared and the volume by the cube. This can provide a large savings in cost, area, and volume. Furthermore, the smaller magnetics may also have smaller intrinsic resistances which help in reducing heat as well as reducing voltage drops with varying current loads that must be regulated out.

Moreover, capacitors in multiple places may not be required to be as large since they are needed to supply energy for shorter amounts of time as compared to conventional SMPS designs. In some embodiments, a properly sized output capacitor combined with a high bandwidth feedback design is utilized to eliminate the use of the LDO 405 which may be a major contributor to power supply inefficiency (heat generation).

Figure 5:
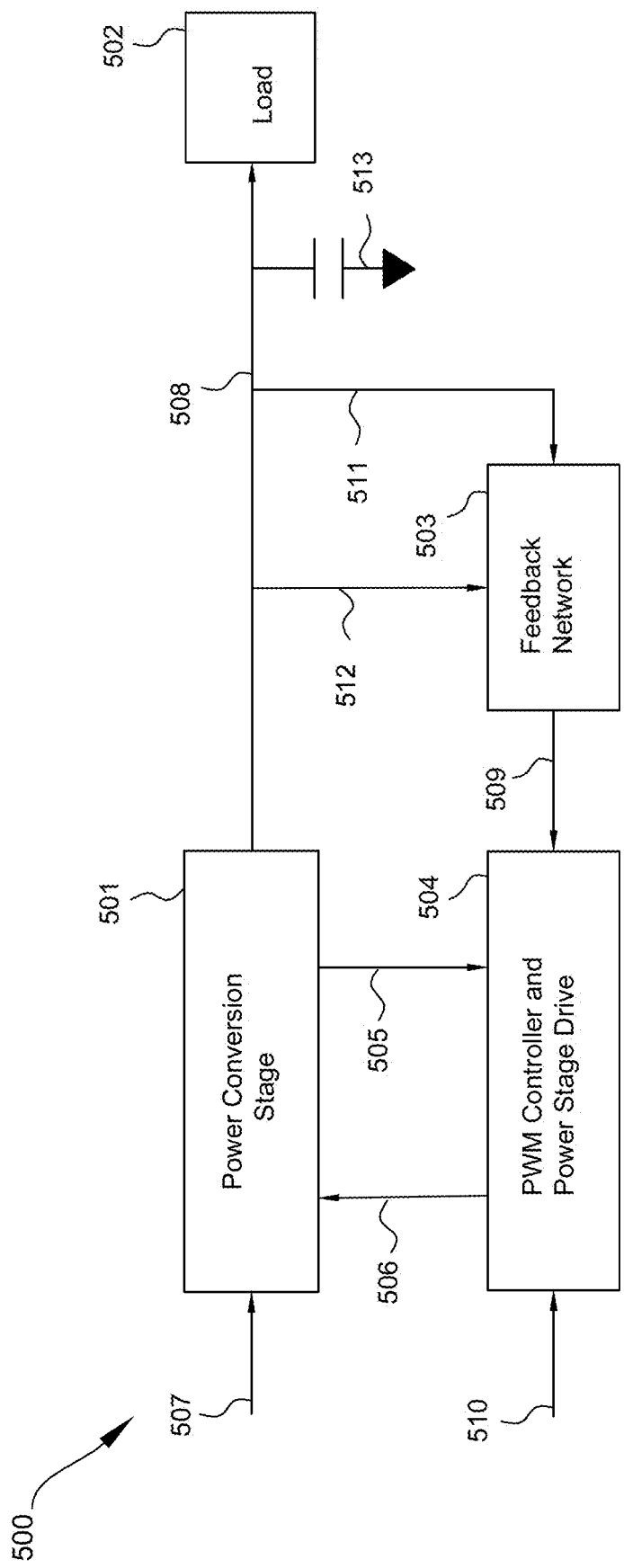
FIG. 5 illustrates the salient blocks of an SMPS according to embodiments of the present technology.

FIG. 5 illustrates the basic components of a generic power supply 500 in accordance with an embodiment of the present technology. Power conversion stage 501 takes input power 507 at an input voltage and converts it to an output voltage 508 delivering power to load 502. In various embodiments, the power conversion stage 501 may be any number of power supply topologies including buck, forward, two-switch forward, half-bridge, full-bridge, push-pull, boost, buck-boost, flyback topologies and many others.

The output voltage 508 is sampled and presented to the PWM controller and power stage drive 504 via a feedback network 503. Feedback network 503 may be an isolated feedback network for use with an isolated power conversion stage 501. Furthermore, feedback network 503 may have a slow response feedback 511 to set the DC value of voltage 508 electrically close to the load (mitigating voltage drops across wires and ground planes) in addition to the high bandwidth feedback 512 of normal operation to regulate load and line variations in the 10 kHz to 100 kHz (and higher) orders of magnitude. Having the high bandwidth feedback path 512 with sufficient bypass capacitance 513 reduces or eliminates the need for a low drop out (LDO) linear regulator just before the load to keep the load voltage within specification which can significantly reduce overall power conversion efficiency. It should be apparent to those of skill in the art that a high frequency feedback path allows capacitor 513 to be proportionately smaller when both are used to stabilize local dynamic current load variations, for example between transmit and receive modes.

The PWM controller and power stage drive 504 modifies the pulse width of the power conversion stage 501 gate drive(s) 506 to maintain output voltage 508 at the desired level. PWM controller and power stage drive 504 not only may utilize voltage feedback signal 509, but may also receive current feedback signal 505 to modify the pulse width of the power conversion stage 501. PWM controller and power stage drive 504 provides the necessary control signals for the power conversion stage topology that are synchronized in part to a digital clock 510 operating at a frequency of FSMPS.

By using a synchronizing clock for each SMPS, each of the various SMPS blocks can operate at the same frequency but at a different phase. This allows the inputs of various SMPS blocks to be tied together since their power draw occurs at slightly different times (and are proportionately lower with the increased frequency) and minimizes their interaction as does the high-speed switching rate, all of which reduces the size and even the need of the input CMF 401 (FIG. 4).

Furthermore, the outputs of two or more (e.g., P) SMPS can be tied together to provide more current without adversely impacting each other. For a balanced distribution of current among the contributing and differently phased SMPS blocks to a single rail, this has the effect of placing most of the energy from the SMPS noise at a P*FSMPS and harmonics of this new fundamental which is much higher and less likely to be a source of imaging artifacts. For practical implementations, this balance is not perfect, but the switching frequency energy that remains at the fundamental FSMPS and harmonics is lowered.

In addition to the particular selection to constrain FSMPS (or its second or third harmonic) to be above the imaging band FXDCR, and FADC tied to being N*FSMPS where N is an integer, the circuits that make up power conversion stage 501 and PWM controller and power stage drive 504 must be able to operate at the selected rate of FSMPS. Operation of the power conversion stage 501 and the PWM controller and power stage drive 504 at 10 MHz or 15 MHz and higher is particularly difficult to do efficiently due to parasitic capacitances of the semi-conductor components.

In some embodiments, the power conversion stage 501 may be implemented as an application specific integrated circuit (ASIC). In other embodiments, it may be more practical (due to varying current and voltage requirements as well as proportionate size of the devices) to implement the power conversion stage 501 with discrete components. It may be useful to choose devices such as MOSFETs with low gate capacitances (which is in tension with high current requirements) and fast rise and fall times, and low variation in propagation times. Thousands of devices exist, and many vendors provide tools to sort based upon (a) average and peak current requirements, (b) gate capacitance, (c) rise and fall transition times, and (d) rise and fall propagation times.

The control of the power conversion stage must be handled carefully when there is more than one switch in the circuit controlling the flow of current. The timing of these control signals from the PWM controller and power stage drive 504 must take into account turn off and turn on times of the particular devices chosen so that no shoot through currents occur, for example, from the input power rail to ground.

Furthermore, the PWM controller and power stage drive 504 may operate at high frequency. Although inherent discrete transistor (e.g., BJT) speed may be fast enough to provide the gate currents required at transition and propagation times of a few nanoseconds to support SMPS operation in the 10 MHz and higher switching frequencies, these are often defeated by running these transistors periodically in and out of saturation. Transistors, particularly BJT transistors, which are otherwise fast enough, become much slower when allowed to saturate. Alternatively, discrete MOSFETs tend to require higher gate currents than desired due to higher gate capacitance and charge characteristics requiring lower impedances connected to the gate or drain.

Typical components of a generic controller 504 for suitable SMPS operation include (a) a sawtooth waveform generator, (b) a comparator used for pulse width modulation (PWM) by comparing the sawtooth waveform with a scaled version of the output voltage, and (c) gate drivers 506 to control the power conversion stage 501 which are often logic circuits that are used to shape the gate drive inputs of power conversion stage 501 to be timed and tailored to prevent shoot through currents.

Typical logic circuit design utilizes putting transistors into saturation for their operation in order to minimize power consumption. However, as stated above, this radically slows the BJT transistor. Since the parasitics of PCB layout are not insignificant, it is difficult to find a discrete typical logic design with sufficient speed. One solution, however, is to keep BJT transistors from entering saturation. This can be accomplished, for example, using the well-known and ubiquitous differential amplifier that is properly DC biased with input signals, intermediate stage signals, and output signals that are AC coupled using series capacitors often in the 1 nF range and smaller, while keeping the AC signal gain low enough to not saturate the transistors. Tail currents as low as 1 mA may be used to power each differential amplifier made of discrete components (ASIC versions may use even lower tail currents). The differential amplifier can be used as (a) a level shifter/inverter, (b) a comparator for the PWM application, (c) an OR/NOR gate by making a double input on one side of the differential amplifier, and (d) an AND/NAND gate by utilizing the well-known derivative of the differential amplifier, the Gilbert cell multiplier or the simpler two-quadrant multiplier operating perhaps between a single power supply rail and ground. In each circuit, the digital signal is simply treated as a large analog signal that is handled in such a way (DC biasing, AC coupling, and gain/offset selection) as to keep the differential amplifier or more complicated Gilbert cell or two-quadrant multiplier transistors out of saturation.

Alternatively, fast logic such as the low-voltage CMOS (LVC) family with sharp rise times and low propagation times and large voltage ranges are another option to the logic gates made with differential amplifiers as noted above. The differential amplifiers described above could still be used as level shifters and comparators.

In some embodiments, ASIC technology may be used, in which the sizes of the transistors are easily controlled, thus allowing control of the saturation properties (e.g. BJT) and gate capacitance and charge properties (e.g. MOSFET) so that logic circuits, level shifters, and comparators are able to operate faster at the same or lower power levels than their discrete implementations owing to the smaller, controlled transistor sizes and the much smaller parasitic capacitances for circuits not having to go out to a pin of a package.

In order to eliminate the LDO 405 (FIG. 4), the feedback network 503 should be sufficiently high band so that the PWM controller and power stage drive 504 can respond to load variations sensed at 512. The size of the output capacitor 513 also plays a key role. This is particularly true when load 502 requires tight control of the voltage applied in order to operate reliably which can easily be as tight as 5% variation on a 1V rail.

There is a minimum size of the output capacitor. It must supply power to support the voltage rail at the largest load between SMPS conversion cycles. This minimum size may be calculated as $$C_{min} = I_{max} \frac{\Delta t}{\Delta V}$$

where Cmin is the minimum output capacitance 513, Imax is the maximum load current, $\Delta V$ is perhaps half of the voltage tolerance and $\Delta t$ is perhaps 1/(2*FSMPS). It would be preferred, however, to increase beyond the minimum as much as is practicable, reserving as much of the allowed tolerance for load and line variations when they are significant.

The bandwidth of the feedback circuit should be able to keep up with the changes of the load or line variations. For example, if the load current reduces to 0.9 Imax, and the output capacitor 513 is sized to be 10× of Cmin from the equation above, then the SMPS has 100 (1/10 load change and 10× Cmin) switching cycles within which to fully correct for the change. This would be on the order of FSMPS/100, or 100 kHz if FSMPS is 10 MHz. Circuit simulation or experimentation may be used to refine the bandwidth requirements for particular applications.

If the line fell from 5 V to 4 V and the output voltage is nominally 1 V, and assuming the output capacitor 513 is sized to be 10× of Cmin from the equation above, then the SMPS has 50 (1/5 line change and 10× Cmin) switching cycles within which to fully correct for that change. This would be on the order of FSMPS/50, or 200 kHz if FSMPS is 10 MHz. Circuit simulation or experimentation may be used to refine the bandwidth requirements for particular applications.

As noted earlier, some embodiments of the present technology enable the control of parasitic capacitances. This may be accomplished using application specific integrated circuit (ASIC) technology wherein signals are able to be routed on the metallization layers and not brought out to the package pins. This is a great advantage over a design that uses transistors in separate packages (discrete transistors) as the packaging and routing itself is a significant source of parasitic components such as inductors and capacitors.

Furthermore, transistors are able to be better tailored to the specific circuit application in an ASIC. For example, transistors can be designed to handle just the current needed allowing them to be smaller than discrete off-the-shelf transistors. This is a significant advantage as typical discrete transistors (applicable for many and varied applications) may handle one to three orders of magnitude more current and so are much larger than needed and consequently contain much larger parasitic capacitances.

Modern transistors and packaging are helpful in bridging the gap between ASIC and discrete implementations. An example of these are GaN field effect transistors (FETs) that are available packaged as passivated bumped die. Not only are these transistors inherently lower in important parasitic characteristics due to modern design, but the elimination of package routing of the signals from the transistor to external pins has lower parasitic characteristics as well.

Another beneficial aspect of the present technology is to enable discrete designs that keep, for example, bipolar junction transistors (BJT) out of saturation. This can be achieved by providing a DC bias to the circuit and AC coupling to the inputs and or outputs. Although this is a well-known design technique used in analog design circuits, in this context it may be used for digital functions instead of the simpler circuits typically used in digital functions that drive transistors into saturation.

FIG. 6A through FIG. 6I illustrate examples of the foregoing concepts applicable for discrete or integrated circuit implementations of SMPS functions. These drawings are merely exemplary and are not to be construed as to limit the scope of this invention to these specific circuit designs. Many other potential implementations following the general principles disclosed herein may be easily conceived of by those of skill in the art. Although examples are given using bipolar junction transistors (BJT), the circuits may instead be designed with many varieties of field effect transistors (FETS) such as JFET, MOSFET, CMOS, GaN FET and so on.

Figure 6A:
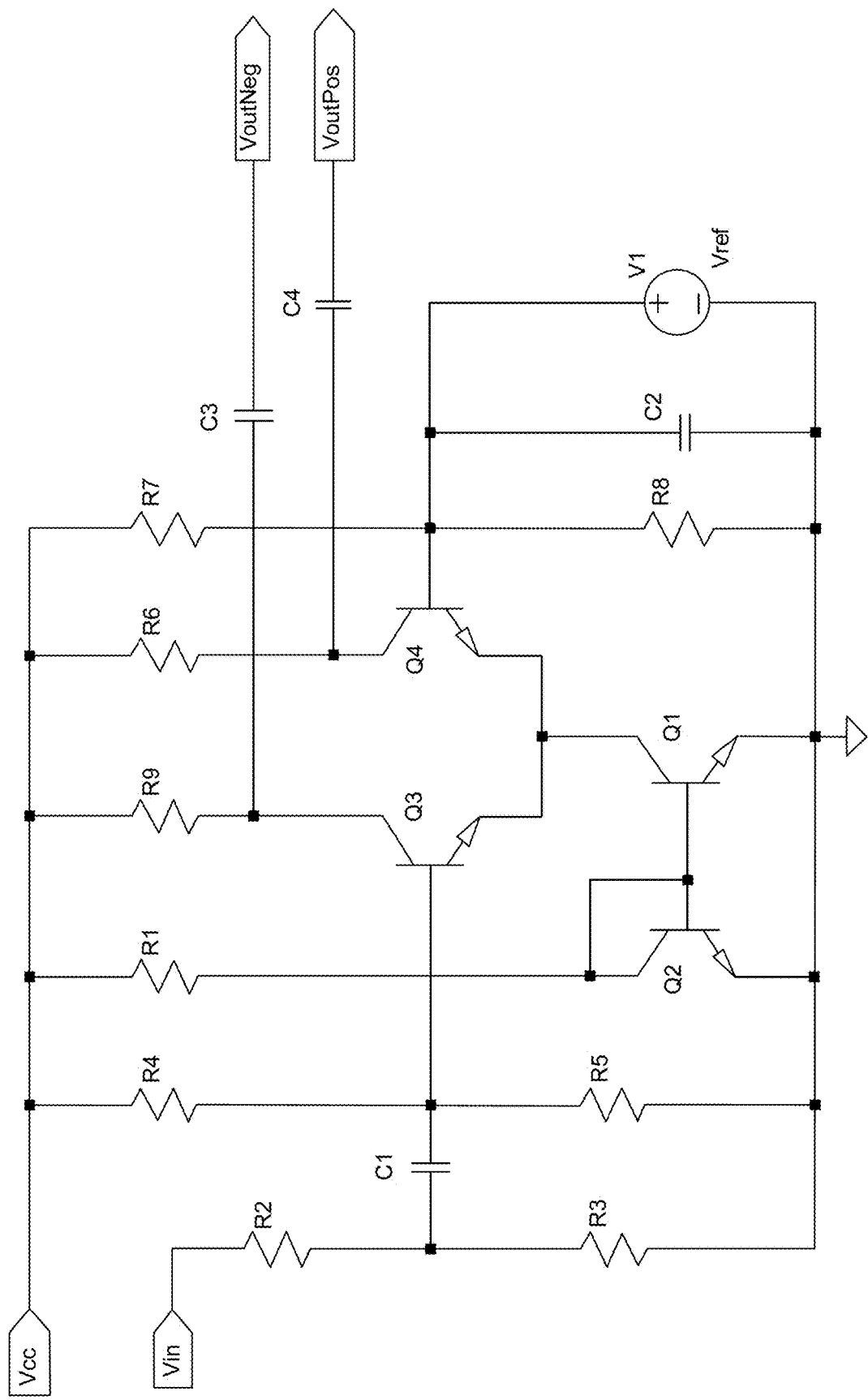
FIGS. 6A-6I illustrate potential discrete implementations of various circuits comprising the functional blocks shown in FIG. 5.

FIG. 6A is an example of a differential amplifier circuit 601. This circuit may be used as a level shifter of sufficient speed to bring signals into or out of the various functions of the SMPS. Q1, Q2, and R1 set the operating current of the differential transistor pair Q3 and Q4 which is important to its speed of operation which depends upon the parasitics of Q3 and Q4. Transistors Q3 and Q4 are selected for their high bandwidth and low parasitic capacitances. R4, R5, R7, and R8 set the DC operating point of Q3 and Q4. C2 may be used to stabilize the voltage at the base of Q4. In lieu of R7, R8, and C2, a reference voltage Vref can be used. Having set the DC bias, the fast input signal Vin is attenuated by the voltage divider formed by R2 and R3. The value of R2 and R3 are selected to control the impedance seen by Vin and set the size of the AC signal. This attenuated signal is AC coupled to Q3 through a small capacitor C1 that is sized commensurate with the signal bandwidth. Resistors R6 and R9 are chosen to provide the correct gain given the bias current set by R1. The resistor values are all chosen so that the power consumption is optimized for the required speed of the signal edges, the output signal swing (VoutPos and/or VoutNeg) is sized to properly operate the subsequent circuitry while not saturating the transistors, particularly Q3 and Q4. Alternatively, R9 and R6 could be replaced by active loads, semiconductor devices for more robust operation. Finally, the output signals are capacitively coupled to the next block, perhaps an emitter follower, so as to not disturb the careful biasing of this circuit as well as the one to follow. In some embodiments, the circuit of FIG. 6A may be used as an inverter circuit (logical NOT) by selecting VoutNeg instead of VoutPos.

Figure 6B:
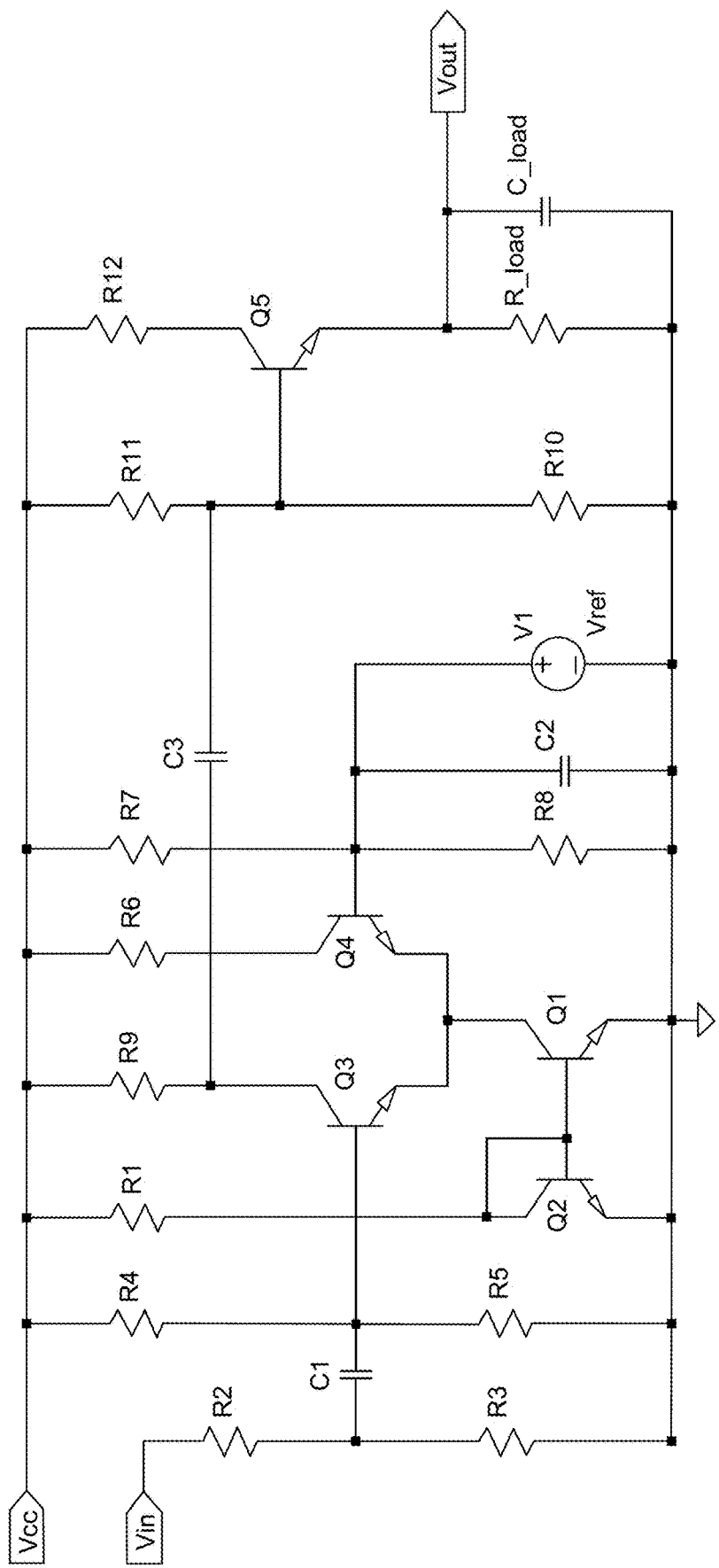

FIG. 6B shows the addition of an emitter follower circuit to the differential amplifier of FIG. 6A. It is also DC biased and AC coupled at its input. It may be used to protect the balanced design of the differential amplifier of FIG. 6A. The DC biasing resistors of R10 and R11 are selected to not interfere with the desired gain set by R9. It is easiest to do this by making the impedances of R10 and R11 large compared to R9. R12 is optional. The buffered signal is then applied to the load as shown in the FIG. 6B as R_load and C_load.

An AC coupled emitter follower of FIG. 6B or the differential amplifier of FIG. 6A may be used as a delay circuit with the output signal being a delayed version of Vin. In some embodiments, the circuit of FIG. 6B may be used as a comparator for fast input signals such as logic levels. R7 and R8 or alternatively Vref can be set for the threshold value to trip the comparator. C2 is helpful to stabilize the voltage.

Figure 6C:
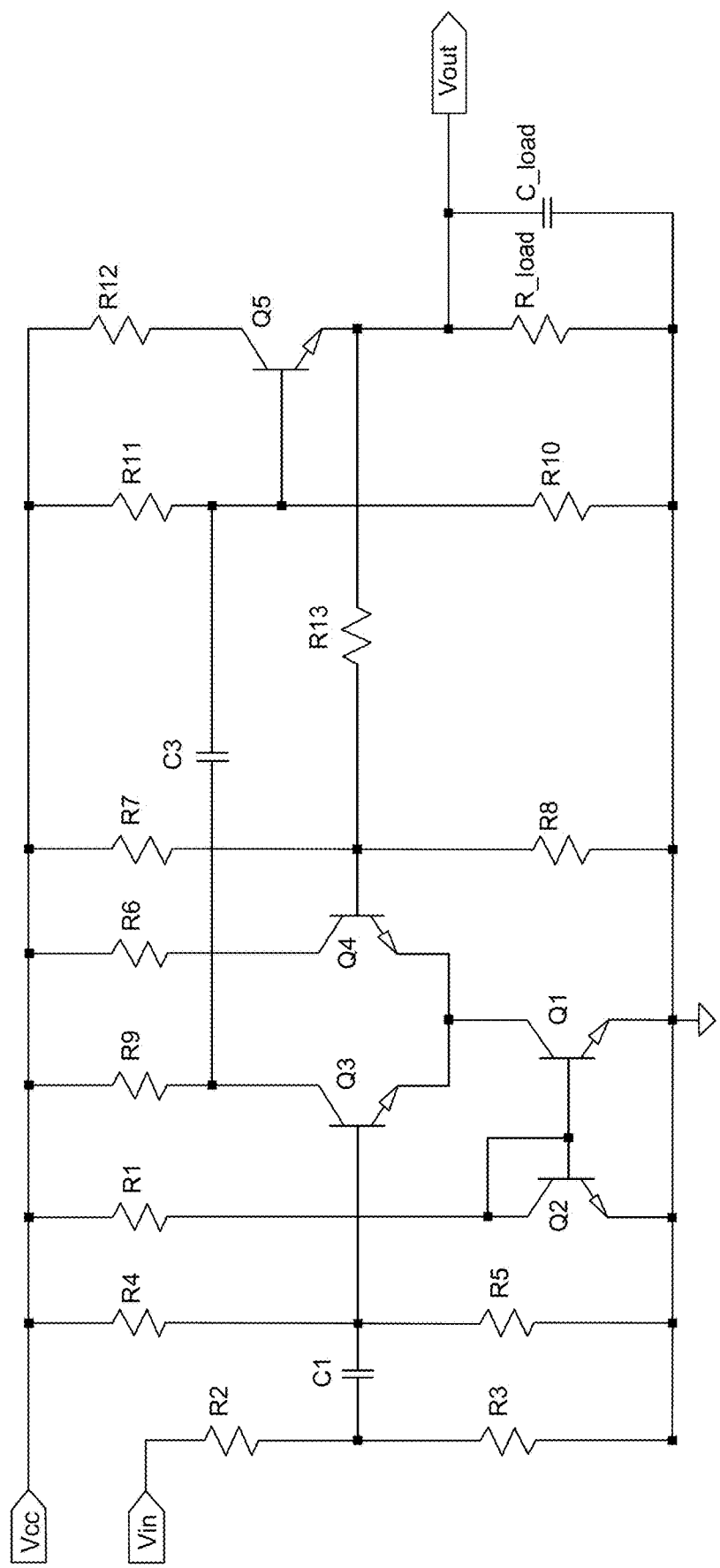

If a comparator is to be used with slower signals having sufficient noise to cause indecision at the threshold level, a resistor R13 can be added between the output and the base of Q4 after removing Vref and C2 turning this comparator into a Schmidt trigger as shown in FIG. 6C. The use of positive feedback for a comparator is well known by those of skill in the art. R13 can be sized to be sufficiently large to not cause the circuit to oscillate.

Figure 6D:
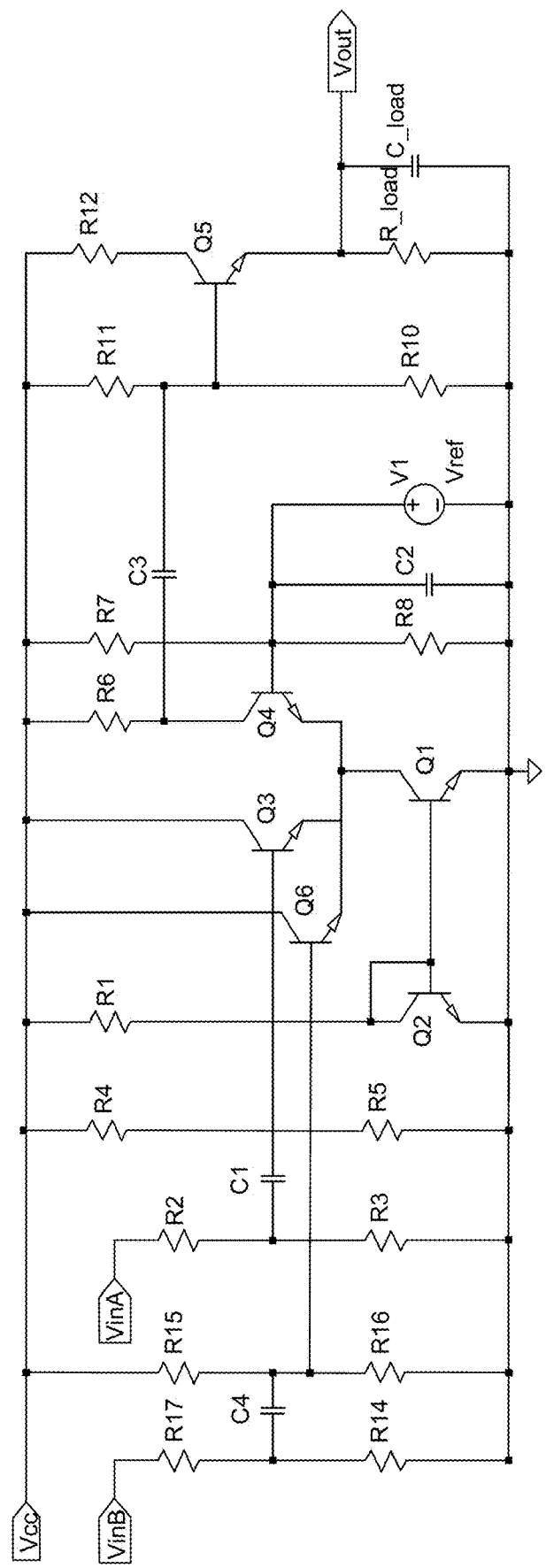

As shown in FIG. 6D, the circuit of FIG. 6A or FIG. 6B may be used as a two-input logical OR gate by adding a second input like Vin, attenuated by its separate voltage divider (like R2 and R3 for Vin), and connected to the base of another transistor parallel to Q3 by a separate capacitor (like C1 does for Vin). VinA and VinB are the two input signals. Vout is the logical OR. Resistors R14, R15, R16, and R17, capacitor C4, and transistor Q6 are added to accommodate another input. A three-input OR gate can be constructed with similar additional parallel legs to the differential amplifier.

Figure 6E:
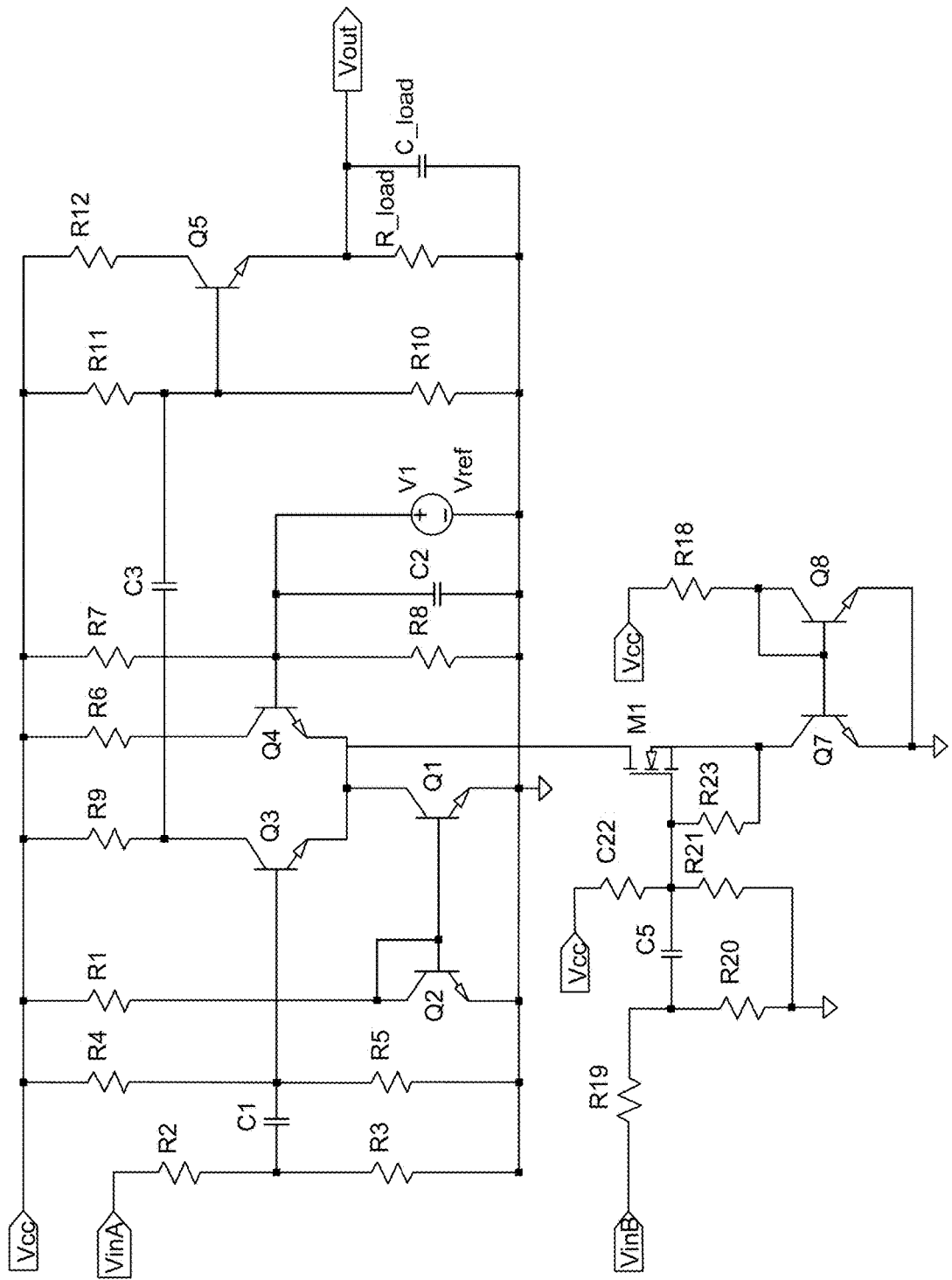

FIG. 6E illustrates a circuit implementing a logical two-input NAND gate, which can be created with the variation in the circuit of FIG. 6B which will be recognized as a two-quadrant analog multiplier by those familiar with analog design. In this implementation, the tail current of the differential amplifier Q3 and Q4 is modified between two levels. A first reduced level is provided by the current source R1, Q1, and Q2. A second larger level is provided by the current source R18, Q7, and Q8. These currents are summed when transistor M1 is turned on. Without the larger current provided by M1 in this way, the voltage at the collector of Q3 never goes low enough (remains at a logic high) as insufficient current flows through R9. With M1 turned on, sufficient current is provided. The current flows through Q3 when VinA is high causing a low voltage and when VinA is low, the current flows primarily through Q4 so that the voltage on the collector of Q3 remains high. Thus, VinA and VinB must both be high to force the output low. Hence, a NAND function.

Figure 6F:
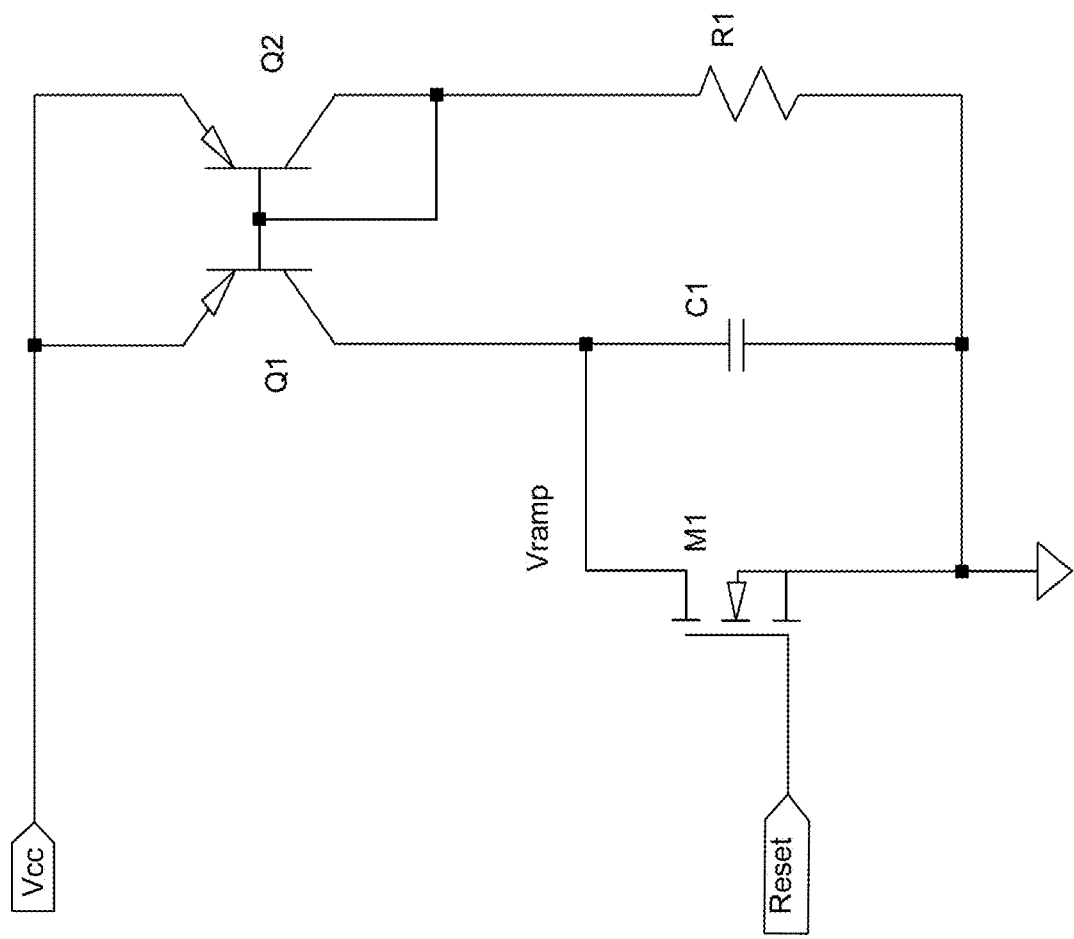

A ramp generator function used to set the variable pulse width to the power conversion gate circuit gate drives in SMPS controllers can be created with the circuit shown in FIG. 6F. In this circuit, the shorting switch M1 is used to bring the ramp voltage down to zero. The parasitic capacitances of this transistor are critical for a MOSFET switch as shown. For a BJT implementation, it is again important that the transistor is kept out of saturation using DC biasing and AC coupling to the reset signal. The Reset signal shown here as active high shorts the capacitor to ground. When released, the current provided by Q1 is determined by the resistor R1 and ratio of areas of Q1 and Q2. The current as well as the capacitor C1 and any parasitics of M1 set the rate at which the ramp voltage rises, clipping just below Vcc.

Figure 6G:
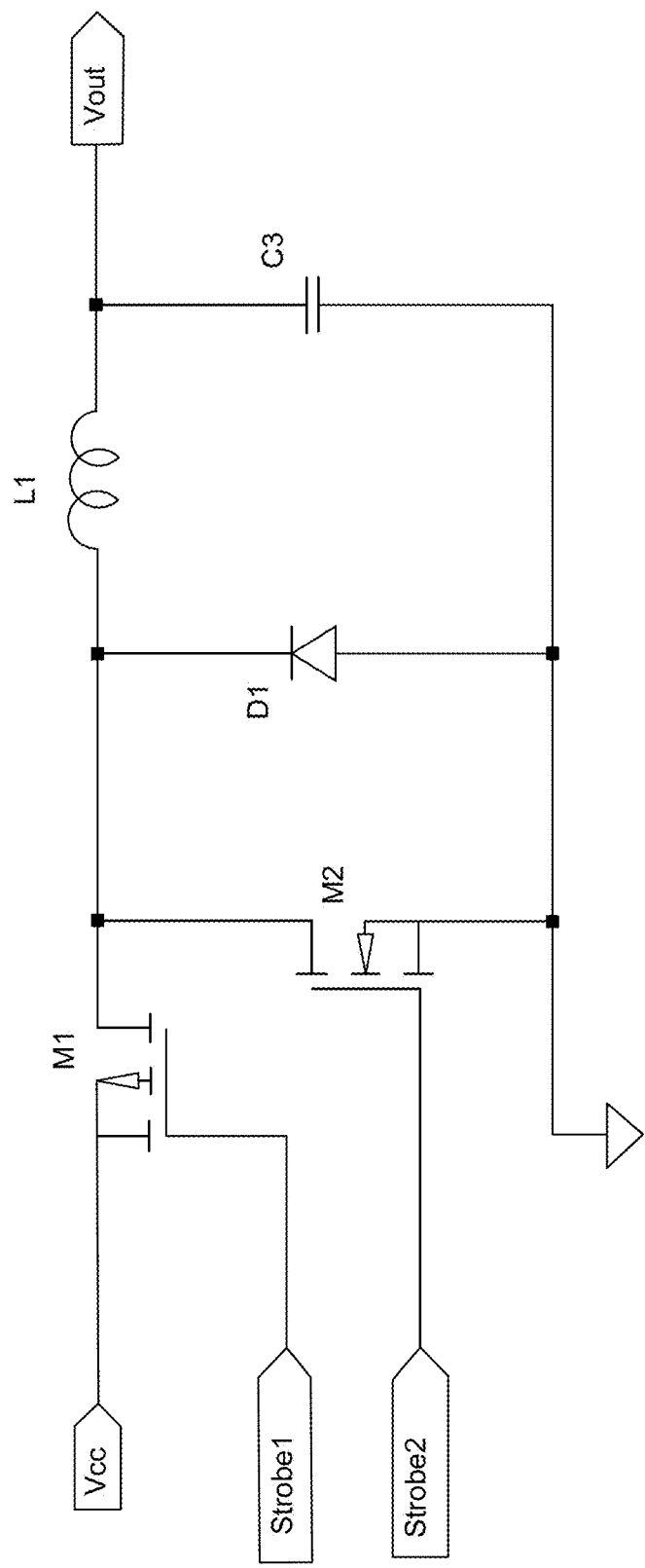

An example power conversion block having two switches is the non-isolated buck topology of FIG. 6G. The efficiency of this circuit can be affected by timing of turning on and off M1 and M2 so that they are never conducting at the same time. This is often difficult to do with a single signal unless M1 and M2 are matched switches with complementary timing properties. Otherwise, the turning off of M2 with Strobe 2 must be advanced sufficiently before M1 is turned on with Strobe1 to account for propagation delays. Similarly, the turning on of M2 must be delayed sufficiently after M1 is turned off for similar reasons. These timing requirements may be accomplished by analog means using ramps and comparators as timers and delays for gate shaping.

Figure 6H:
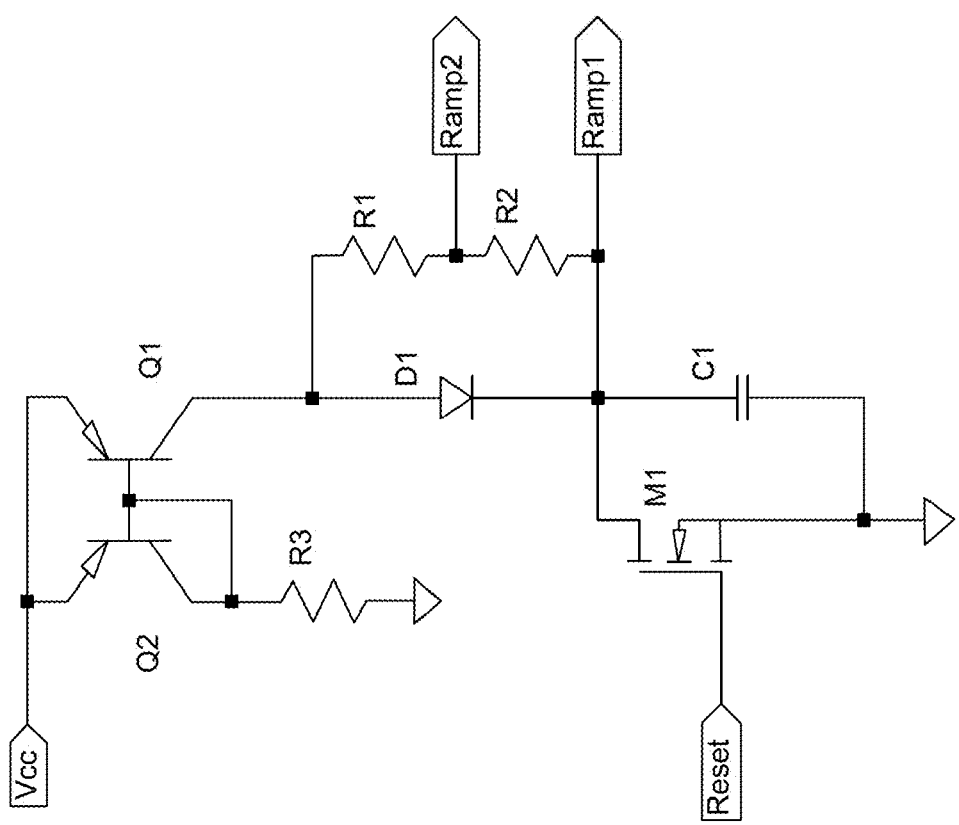

When the ramp generator signal of FIG. 6F exceeds the value of the feedback signal proportional to the output voltage, the power conversion MOSFET M1 of FIG. 6G is placed into conduction. M1 of FIG. 6G turns off at the end of the $F_{SMPS}$ clock cycle when the ramp generator signal of FIG. 6F is reset and falls below the feedback signal. In order to advance the timing of turning off M2 of FIG. 6G so as to avoid shoot through current (off delays are often longer than on delays), it is helpful to generate a parallel ramp function for use in turning off M2 of FIG. 6G before M1 of FIG. 6G is turned on. (Alternatively, D1 in FIG. 6G can be used in place of M2 for this type of SMPS with some loss of efficiency or with M2 to alleviate timing requirements for operation of M2.) The technique illustrated in FIG. 6H is one way to do so. The difference between FIG. 6F and FIG. 6H is the insertion of a diode (D1) or some other fixed voltage source (e.g. band gap circuit or reference voltage circuit) in line with the current source (Q1, Q2, and R3 of FIG. 6H) to the charging capacitor (C1). The voltage across D1 is relatively constant at perhaps 0.7 V. If Vcc is about 7 volts, then the voltage across D1 is approximately 10% of the ramp voltage, or equivalently 10% of the time of the time duration of the ramp function. A fraction of this voltage, or equivalently time, by the resistor divider R1 and R2 of FIG. 6H can be used to dial in the precise timing needed. Thus, by using the time at which Ramp1 exceeds the feedback voltage to turn on M1 of FIG. 6G and using the time at which Ramp2 exceeds the same feedback voltage to turn off M2 of FIG. 6G, shoot through can be reduced or eliminated by ensuring that M2 of FIG. 6G turns off before M1 of FIG. 6G turns on.

MOSFETs such as M1 and M2 in FIG. 6G can provide very low resistance paths which makes power conversion efficient. However, typically these devices have significant gate capacitance or junction charge requirements which require high current capabilities that logic circuits may not inherently have. One effective solution to provide high current capability is to place a class B BJT transistor output stage such as Q3 and Q4 of FIG. 6I before the gates of M1 and M2 of FIG. 6G. Since the corresponding gate control voltage swing is reduced by about a diode drop to the inside of the Vcc and GND rails, the gate-source threshold voltage of M1 and M2 of FIG. 6G must be greater than the diode drop of Q3 or Q4 in FIG. 6I.

Figure 6I:
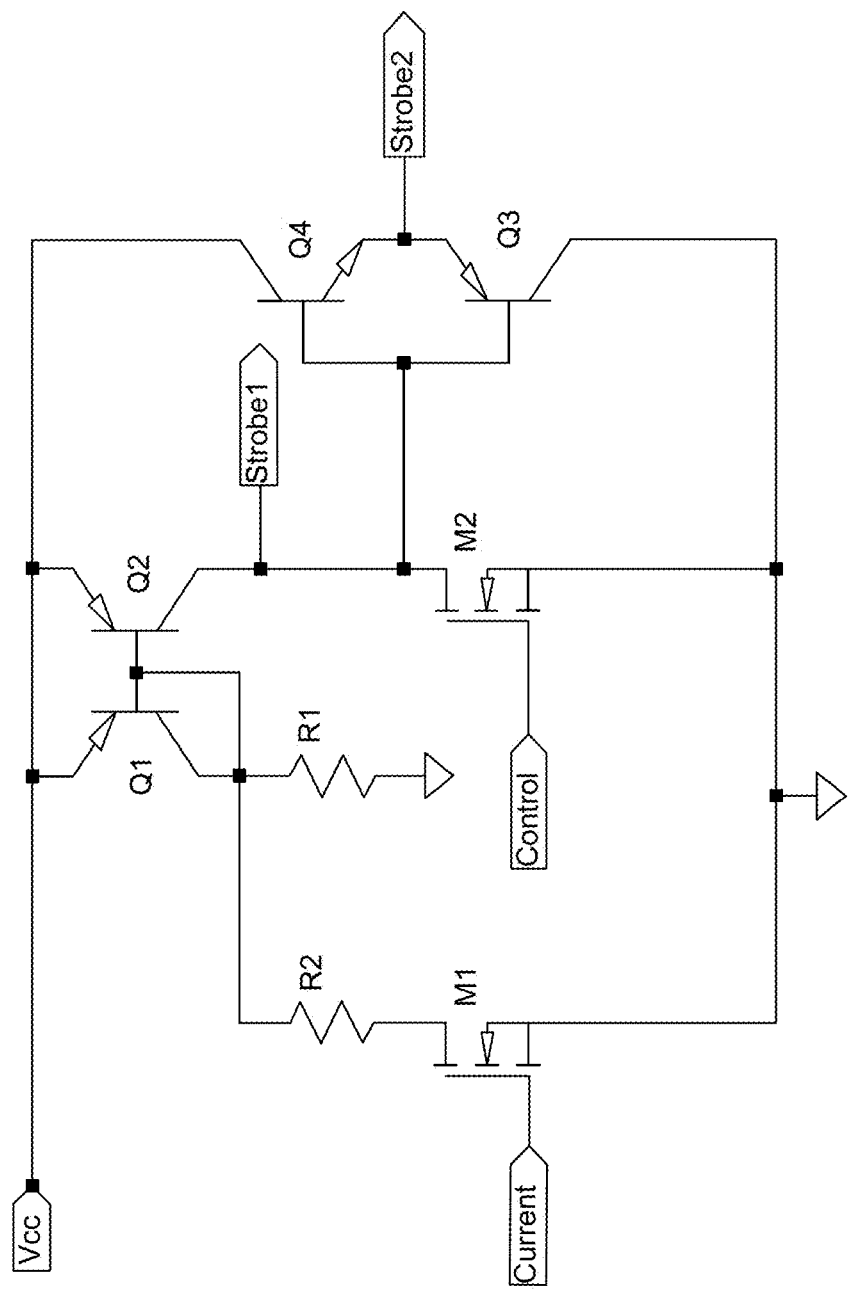

For some MOSFETs such as M1 and M2 in FIG. 6G, this still is not enough. Thus, another smaller MOSFET, M2 in FIG. 6I, with much lighter drive requirements such as a GaN FET may be used. This smaller MOSFET may perform well when a logic "one" signal is applied to the CONTROL terminal. This quickly shorts the drain of M2 in FIG. 6I to ground causing the inputs of Q3 and Q4 to be driven low causing Strobe2 to go low very quickly. However, when a logic "zero" signal is applied to the CONTROL terminal, it is the impedance from Vcc to the drain of M2 in FIG. 6I that controls the rise time of Strobe2. Although a resistor could be used, it may be advantageous to use a current source structure (Q1, Q2, and R1 of FIG. 6I) as an active load. The value of R1 can be dialed in to provide sufficient current to greatly improve the rise time of Strobe2. However, this current source is a constant load, and since it may need to be relatively high, it can significantly reduce the efficiency of the power supply overall. To alleviate that, another switch, M1 of FIG. 6I, is provided which places R2 in parallel with R1. R2 may be a very low value so that the current source provides a high level of current. R1 may be a relatively large value for a small amount of current to hold voltages during the quiescent part of the cycle or even absent altogether. In this way, high current can be provided to drive the bases of Q3 and Q4 toward Vcc during the transition time only and not during the whole time. In this way, the efficiency burden of the high current source can be mitigated by a duty cycle. Thus, in FIG. 6I, just before the Control signal of M2 goes low, the control logic drives the Current input high putting a relatively low value of R2 in the control path of the current mirror Q1 and Q2 greatly increasing the current and lowering the impedance to the Vcc rail. The high current (low impedance path) to Vcc provided by Q2 drives the bases of Q3 and Q4 high causing a very fast rise time on Strobe2. Once this transition of Strobe2 from low to high is completed, the Current control signal rises to disconnect R2 and reduce the quiescent current to that corresponding to R1. In this way, by means of a pulsed current source, a fast rise time on Strobe 2 can be acquired while minimizing the overall current draw throughout the power conversion cycle.

In some cases, the Class B output stage is not needed to sufficiently control the MOSFET gates of FIG. 6G. In this case, the Class B output stage is eliminated, and Strobe 1 in FIG. 6I is used instead of Strobe 2.

Most SMPS topologies require one or two switch drivers to control the larger MOSFETs used. Given there are two switch drivers needed, two independent circuits such as that shown in FIG. 6I are needed. Each of these control signals have a rising edge and a falling edge that need to have quick transition times that are precisely placed with respect to one another. The falling edge of the Control signal of FIG. 6I may need to be bracketed by a precisely timed rising and falling edge of the Current signal of FIG. 6I in order for the transition time of Strobe2 to be minimized without greatly harming overall power conversion efficiency. This approach can be extended to any number of switches.

Timing of some or all of these edge transitions can be performed with fast comparators such as the ones described above, some comparators in discrete packages, or ones designed for ASICs. They may have relatively fast rise, fall, and propagation times on the order of 5% of the FSMPS time period. At one input, these comparators each have a ramp signal such as from Ramp1 or Ramp2 in FIG. 6H. The other input of the comparators are either tied to a fixed reference voltage derived from the power rail by means of a voltage divider (or some other fixed voltage circuit such as a regulator or voltage multiplier) or a variable input such as the feedback voltage derived from the output for its regulation. Simple logical combinations of these comparator outputs are used (along with a reset signal that occurs at the FSMPS rate) to achieve the edge transitions required for any SMPS topology need.

The same techniques described herein may be applied to any of the power supply conversion topologies to make them work at a sufficiently high frequency. These include, but are not limited to, the buck converter, forward converter, two-switch forward converter, half-bridge converter, full-bridge converter, push-pull converter, boost converter, buck-boost converter, and flyback converter.

The foregoing descriptions of FIG. 6A through FIG. 6I are exemplary. There are other well-known circuit topologies that may be used for these same functions which are subsumed under the scope of this disclosure. The examples described herein illuminate certain functions useful for creating an SMPS controller of the speed required, including simple logic gates (which can be made from combinations of NOT, OR, NAND presented herein), ramp generators, and comparators, any or all of which may be combined in a number of ways to shape the pulses which ultimately are used to drive the gates of the transistors used as power conversion switches.

In some embodiments, these circuits may operate at rates of about 10 MHz or more. This may be difficult to achieve with discrete transistors, due primarily to the parasitic capacitances. Accordingly, it can be useful to mitigate the speed limiting effect of these parasitics. This may be best accomplished by implementation into an ASIC. If done with discrete transistors, however, care should be taken to keep them out of saturation.

Modern digital integrated circuits such as field programmable gate arrays (FPGAs) are fast enough such that they can perform the same functions as their analog counterparts. Counters may be used in place of analog ramps. Counters and digital comparators or shift registers can be used in place of analog delays and timing functions. Analog-to-digital converters (ADC) translating the feedback signal to digital words can be used as the input to a look up table (LUT) that governs the pulse width of the power conversion gate. Alternatively, math and logical operators can compute the pulse length. The relative timing of the various power conversion transistor gate drive pulses are easily constructed with standard adders, subtractors, and comparators of digital construction.

Crucial to the success of a digital approach is that the resolution of the digital operations should be substantially faster (e.g. 10× or more) than the power conversion clock frequency. The second crucial aspect is that in keeping with this embodiment, the digital clock that is substantially faster than the power conversion frequency should be in phase with the signal ADC and an integer multiple of it as noted much earlier in this disclosure.

Rather than a fully digital implementation, a combined analog and digital approach may be used. The analog circuits described previously in which logic is implemented using a differential amplifier may more easily be implemented with individual digital integrated circuit gates using a logic family (e.g. the LVC digital family) supporting the voltage and speed demands. Thus, ramps and comparators may be used to construct signals from which gate drive pulses may be shaped using integrated circuits offering fast digital gates to do the logical combinatorial manipulation. Where the digital family is not compatible with the voltage levels of either the inputs or the outputs, the level shifters disclosed herein may be used for the conversion.

Ramp generators do not need to be strictly linear. They are simply periodic waveforms that return to a preset value either high or low when reset at the clock rate. Substantially, the rest of the waveform is monotonically decreasing or increasing towards a low or high value, respectively. They are there so that timing points can be selected by means of other functions such as comparators and voltage references. So, for example, an exponential shape from an RC network could be used instead of a current source and capacitor as previously described.

Conclusion

Although many of the embodiments are described above with respect to systems, devices, and methods for powering ultrasound imaging systems, the technology is applicable to other applications and/or other contexts, such as powering other imaging modalities (e.g., MRI machines), or power supplies for other imaging or non-imaging contexts. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-6I.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Unless otherwise indicated, all numbers expressing frequencies, voltages, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The invention claimed is:

1. An imaging system comprising:
    a transducer having a sensitivity band with a lower limit $F_{XDCR-LOWER}$;
    signal processing circuitry configured to receive output signals from the transducer; and
    a switched mode power supply configured to provide power to one or more components of the signal processing circuitry, the switched mode power supply configured to operate at a switching rate $F_{SMPS}$;
    wherein $F_{SMPS}$ is within about 1 MHz of $F_{XDCR-LOWER}$.

2. The system of claim 1, further comprising an analog-to-digital converter (ADC) configured to receive and digitize the output signals from the signal processing circuitry, the ADC configured to operate at an ADC rate $F_{ADC}$, wherein $F_{ADC}$ is an integer multiple of $F_{SMPS}$.

3. The system of claim 1, wherein the ADC is synchronized with the switched mode power supply.

4. The system of claim 1, wherein the signal processing circuitry comprises at least one of: a transmit/receive switch or an amplifier.

5. The system of claim 1 herein, wherein $F_{SMPS}$ is greater than a bandwidth of the transducer.

6. The system of claim 1, wherein the transducer has a bandwidth of between about 1 and about 15 MHz.

7. The system of claim 1, wherein $F_{SMPS}$ is greater than a bandwidth of the transducer.

8. The system of claim 1, wherein the imaging system is one of: an ultrasound imaging system, a magnetic resonance imaging (MRI) imaging system, a positron emission tomography (PET) imaging system, a computed tomography (CT) imaging system, or an X-ray imaging system.

9. A switched mode power supply controller comprising:
    a sawtooth waveform generator configured to output waveforms having a frequency of about 5 MHz or greater; and
    a gate driver configured to output gate drive signals that:
        (i) have a rise or fall time of less than about 10 nanoseconds,
        (ii) have a pulse repetition frequency of about 5 MHz or greater, or
        (iii) both (i) and (ii).

10. The controller of claim 9, wherein the sawtooth waveform generator comprises an analog sawtooth waveform generator or a digital sawtooth waveform generator.

11. The controller of claim 9, wherein the controller is configured to receive a feedback input signal.

12. The controller of claim 11, wherein the feedback input signal comprises a voltage feedback signal from a feedback network.

13. The controller of claim 11, wherein the feedback input signal comprises a current feedback signal from a power conversion stage.

14. A method comprising:
    obtaining image data via one or more imaging transducers having a sensitivity band with upper limit of $F_{XDCR-UPPER}$;
    processing the image data via signal processing circuitry; and
    powering at least a portion of the signal processing circuitry via a switched mode power supply operating at a switching rate $F_{SMPS}$,
    wherein $N*F_{SMPS}$ is greater than $F_{XDCR-UPPER}$, and wherein N is 1, 2, or 3.

15. The method of claim 14, wherein the signal processing circuitry comprises at least one of: a transmit/receiver switch operably coupled to the transducer(s), an amplifier, or an analog-to-digital converter.

16. The method of claim 14, wherein processing the image data via the signal processing circuitry comprises receiving and digitizing image data signals via an analog-to-digital converter (ADC) operating at an ADC rate $F_{ADC}$, wherein $F_{ADC}$ is an integer multiple of $F_{SMPS}$.

17. The method of claim 14, wherein the one or more imaging transducers comprise one or more ultrasound transducers.

18. The method of claim 14, wherein the signal processing circuitry comprises an analog-to-digital converter (ADC), the method further comprising operating the ADC in synchrony with the switched mode power supply.

19. The method of claim 14, wherein the one or more imaging transducers have a bandwidth of between about 1 and about 15 MHz.

20. The method of claim 14, wherein the one or more imaging transducers have a bandwidth of greater than about 5 MHz.

* * * * *